(12) United States Patent
Theze et al.

(10) Patent No.: US 6,168,785 B1
(45) Date of Patent: Jan. 2, 2001

(54) BIOLOGICAL APPLICATIONS OF NEW PEPTIDES OF IL-2 AND DERIVATIVES AND USE AS THERAPEUTIC AGENTS

(75) Inventors: Jacques Theze, Paris; Ralph Eckenberg, Germain en Laye; Jean-Louis Moreau, Paris; Jean-Claude Mazie, Asnières-sur-Seine, all of (FR)

(73) Assignee: Institut Pasteur, Paris (FR)

( * ) Notice: Under 35 U.S.C. 154(b), the term of this patent shall be extended for 0 days.

(21) Appl. No.: 09/116,594

(22) Filed: Jul. 16, 1998

(51) Int. Cl.[7] .................................................. A61K 38/20

(52) U.S. Cl. .................. 424/85.2; 514/2; 514/8; 514/12; 514/885

(58) Field of Search ............................ 514/2, 8, 12, 885; 424/85.1, 85.2

(56) References Cited

U.S. PATENT DOCUMENTS

| | | | |
|---|---|---|---|
| 4,690,915 | * | 9/1987 | Rosenberg ............................ 514/2 |
| 4,879,111 | * | 11/1989 | Chong ............................... 424/85.2 |
| 5,336,488 | * | 8/1994 | Daley et al. ...................... 424/85.2 |

OTHER PUBLICATIONS

Bernstein et al. (1995) Blood, vol. 86, No. 9, pp. 3287–3294.

\* cited by examiner

*Primary Examiner*—Prema Mertz
(74) *Attorney, Agent, or Firm*—Oblon, Spivak, McClelland, Maier & Neustadt, P.C.

(57) ABSTRACT

The invention relates to the use as therapeutic agents of IL-2 peptides and derivatives having biological activity and anti-IL-2 antibodies which mimic or modulate the biological activities of IL-2. The invention also relates to DNA sequences encoding the IL-2 peptides, and to methods of using the IL-2 peptides and derivatives and anti-IL-2 antibodies to modulate or mimic or antagonize the biological activities of IL-2 in vivo and to assay for the presence and activity of the IL-2 receptor.

6 Claims, 24 Drawing Sheets

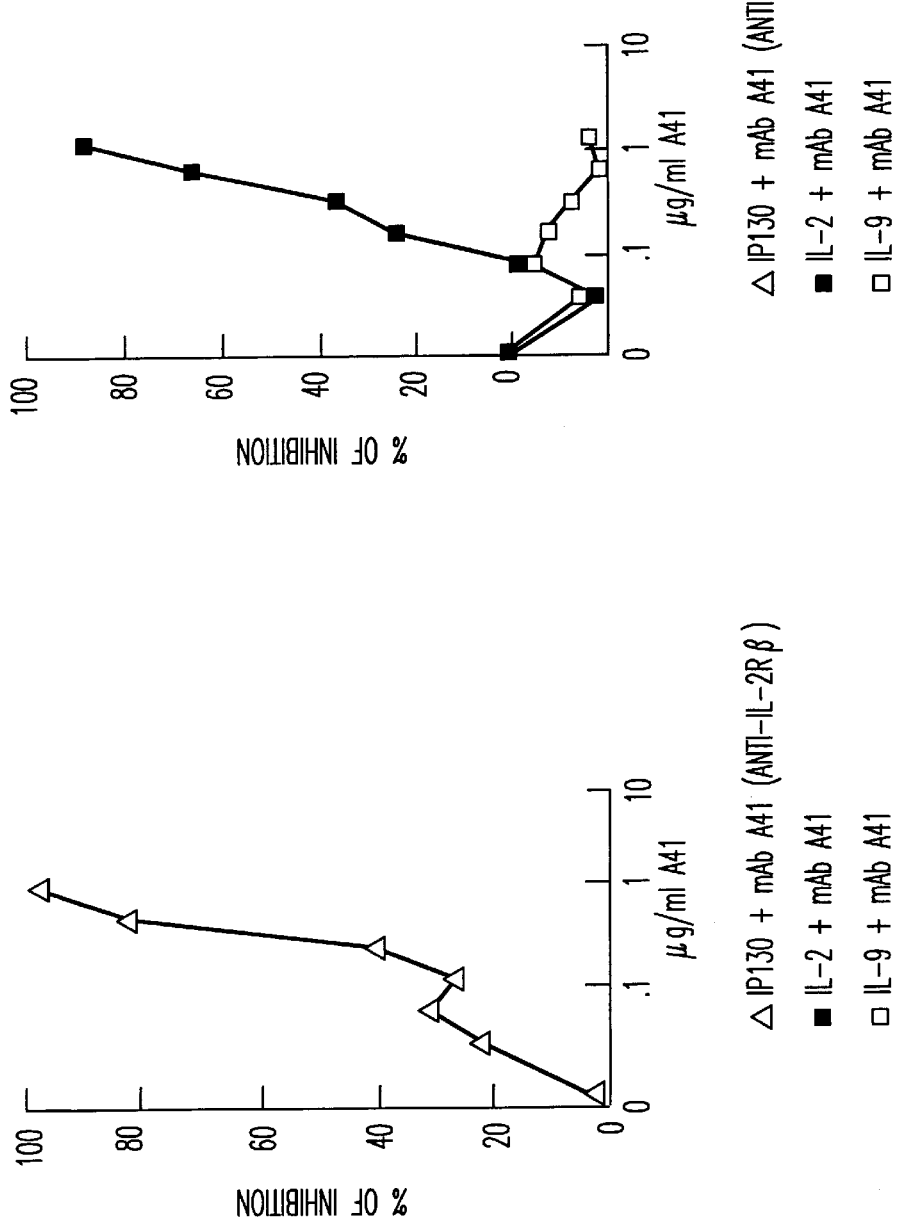

| Sequence | % HELIX (CIRCULAR DICHROISM) | MAIN MOLECULAR SPECIES | ACTIVITY |
|---|---|---|---|
| APTISSSTKKTQLQLEHLLLDLQMILNGINN (1-30) | 50% (150 @ 30μM) 35% (4μM) | TETRAMER (4M–8M, Kd=30–100μM) /OCTAMER | +++ |
| (1-30) | 22% (150 @ 30μM) | DIMER (1M–2M,Kd=0.2μM) /TETRAMER (2M–4M,Kd=100μM) | ++ |
| (1-22) | <2% | | – |
| (1-15) | 0% | DIMER (1M–2M,Kd=50μM) (2M–4M,Kd=1.4mM) | – |
| (5-20) | 0% | DIMER (1M–2M,Kd=113μM) | – |
| (10-20) | 0% | MONOMER | ND |
| (20-30) | <5% | MONOMER | + |

IL-2 RECEPTOR AND ITS MAJOR SIGNAL TRANSDUCTION PATHWAY    MODEL OF TRANSDUCTION PATHWAY INDUCED BY IP130

NK CELLS (CD56⁺) ENTERING IN S+G2/M PHASES AFTER IP130 STIMULATION (SYNERGY WITH IL-2)

| TREATMENT | | | J31 | J32 | J33 |
|---|---|---|---|---|---|
| IL-2 50 nM | | | 14 | 12 | 14 |
| | IP130 | 60μM | 0 | 17 | ≤5 |
| | IP130 | 120μM | 0 | 14 | <5 |
| IL-2 50 nM + | IP130 | 60μM | 26 | 21 | 7 |
| IL-2 50 nM + | IP130 | 120μM | 28 | 28 | 28 |

*FIG. 15*

BIOLOGICAL APPLICATIONS OF NEW PEPTIDES OF IL-2 AND DERIVATIVES AND USE AS THERAPEUTIC AGENTS

BACKGROUND OF THE INVENTION

1. Field of the Invention

The present invention relates to the use as therapeutic agents of IL-2, IL-2 peptides and derivatives which act as interleukin-2 (IL-2) agonists and antagonists, and to methods of modulating IL-2 activity.

2. Discussion of the Background

Interleukin-2 (IL-2) is the main growth factor of T lymphocytes (Thèze et al. 1996, Immunol. Today 17:481–486). By regulating T helper lymphocyte activity IL-2 increases the humoral and cellular immune responses. By stimulating cytotoxic CD8 T cells and NK cells this cytokine participates to the defense mechanisms against tumors and viral infections. IL-2 is used in therapy against metastatic melanoma and renal adenocarcinoma. IL-2 is used in clinical trials in many forms of cancer (Lotze and Rosenberg 1988, Interleukin 2 as a Pharmaclologic Reagent. in Interleukin 2, K. A. Smith, Academic Press: p. 237–89). It is also used in HIV infected patients and leads to a significant increase in CD4 counts (Kovacs et al. 1996, New Engl. J. of Medicine 1350–6).

Human IL-2 is a protein of 133 amino acids (aa) composed of four α helices connected by loops of various length; its tridimensional structure has been established. IL-2R is composed of three chains α, β and γ. IL2Rα controls the affinity of the receptor. IL-2Rβ and IL-2Rγ are responsible for IL-2 signal transduction. The different molecular areas of IL-2 interacting with the three chains of the IL-2 R have been defined. More specifically it has been determined that a helix A as well as the $NH_2$ terminal area of IL-2 (residues 1 to 30) control the interactions IL-2/IL-2Rβ (Eckenberg et al. 1997, Cytokine 9:488–98): IL-2Rβ chain is the most important in IL-2 signaling (Thèze et al. 1990).

The effects of human interleukin-2 (IL-2) on its target cells are mediated through specific cell surface receptors (IL-2R) (Taniguchi et al. (1983) Nature 302:305–310; Robb et al. (1984) Proc. Natl. Acad. Sci. USA 81:6486–6490; Smith K A. 1988a. Interleukin-2; Smith K A (1988b) Science 240:1169–1176). IL-2R comprises at least three subunits encoded by different genes (Minami et al. (1993) Annu. Rev. Immuniol. 11:245–267; Taniguchi et al. (1993) Cell 73:5–8). The first component to be identified, IL-2Rα, is a 55 kDa protein that binds IL-2 with a $K_d$ of≅10 nM (Uchiyama et al. (1981) J. Immunol. 126:1293–1297; Leonard et al. (1984) Nature 311:626–631). The role of IL-2Rα (Kumar et al. (1987) J. Immunol. 139:3680–3684) and the influence of IL-2 on IL-2Rα gene expression have been studied (Bismuth et al. (1985) Eur. J. Immunol. 15:723–727; Froussard et al. (1991) Mol. Immunol. 28:87–93). The second IL-2R component, IL-2Rβ is a 75 kDa protein with a large intracytoplasmic domain (286 aa) (Teshigawara et al. (1987) J. Exp. Med. 165:223–238; Hatakeyaina et al. (1989) Science 244:551–556; Tsudo et al. (1989) Proc. Natl. Acad. Sci. USA 86:1982–1986). The last component to be identified, IL-2Rγ, is a 64 kDa protein (Takeshita et al. (1992) Science 257:379–382; Ishii et al. (1994) Int. Immunol. 6:1273–1277). IL-2Rβ and IL-2Rγ belong to the hematopoietin receptor family whereas IL-2Rα belongs to another family of molecules (Thèze J (1994) Eur. Cytokine Netw. 5:353–368). In the mouse system all three chains are required to form a functional receptor (Moreau et al. (1995a) J. Immunol. 155:3401–3408; Chastagner et al. (1996) Eur. J. Immunol. 26:201–206). In the human system two receptors are functional. When associated, human IL-2Rβ plus IL-2Rγ form an intermediate affinity receptor with a $K_d$ of≅1 nM, whereas expression of all three chains leads to the formation of a high affinity IL-2R ($K_d$≅10 pM).

The structure of IL-2 (MacKay D (1992) Science 257:410–413) is composed of a compact core bundle of four antiparallel α helices connected by three loops (FIG. 1). Some of the interactions between IL-2 and IL-2Rα (Sauv et al. (1991) Proc. Nati. Acad. Sci. USA 88:4636–4640; Wang et al. (1995) Eur. J. Immunol. 25:1212–1216) and IL-2Rγ subunits (Voss et al. (1993) Proc. Natl. Acad. Sci. USA 90:2428–2432; Buchli et al. (1993) Arch. Biochm. Biophys. 307:411–415) have been elucidated, but less is known concerning IL-2/IL-2Rβ interaction, despite the fact that IL-2Rβ chain plays a very critical role in signal transduction (Taniguchi T (1995) Science 268:251–255).

It has been shown that one substitution Asp20 by Lys (mutant D20K) prevents binding to IL-2Rβ (Collins et al. (1988) Proc. Natl. Acad. Sci. USA 85:7709–7713). In a recent report the role of the sequence (Leu17, Leu18, Leu19, Asp20, Leu21) from IL-2α helix A, in IL-2/IL-2Rβ interactions was analyzed by cassette mutagenesis (Berndt et al. (1994) Biochemistry 33:6571–6577). However the data were difficult to interpret since most of the proteins produced have multiple mutations inside and outside of the sequence of interest. Only one analog with a single mutation was studied (L21V). More surprisingly it was reported in this study that deletion of the segment spanning residues 17–31 (Del1) gives a protein with full agonist activity.

IL-2 peptides and derivatives were described in Cytokine (1997) 7:488–498, but were not tested in an in vitro system for biochemical activity such as cytokine activity, and in particular for IL-2-like activity.

In view of the aforementioned deficiencies attendant with the prior art analysis of IL-2 agonists and antagonists, as well as with methods of modulating IL-2 activity therewith, it is clear that there exists a need in the art for the same.

SUMMARY OF THE INVENTION

Accordingly, one object of this inventions to provide compositions having an IL-2-like activitv and methods for their use as therapeutic agents. The applications of such recombinant, synthetic or hybrid peptides are thus one object of the invention. These compositions are defined as having the following characteristics: a) containing one or more peptides at least five amino acids in length; and b) inhibiting or mimicing the binding of α helix A of interleukin-2 (IL-2) to a β subunit of an IL-2 receptor (IL-2R).

Another object of the invention is the use of a purified peptide having the following characteristics: a) the peptide is at least five amino acids in length; b) the peptide binds to β subunit of an IL-2 receptor (IL-2R); and c) the peptide induces phosphorylation of the β subunit of the IL-2R.

A further object of the invention concerns the preparation of the antibodies which recognize the peptides of the invention, and the therapeutic use of these antibodies.

A further object of the invention is the use of DNA sequences encoding the peptides of the invention and their derivatives. Such DNA fragments are useful for gene therapy among other applications. The use of a DNA of the following sequence

ATG GCT CCG ACG AGC AGC TCC ACC AAG AAA
ACC CAG CTC CAG CTC GAA CAC CTG CTG

CTG GAC CTG CAG ATG ATC CTG AAC GGT ATC AAC AAC (SEQ ID NO:1) is one particular object of the invention.

Yet another object of the invention is to provide a method for detecting the activity of an IL-2-like peptide, wherein the IL-2 activity is measured by the binding of the IL-2R to the peptide having the IL-2 agonist or antagonist activity.

A still further object of the invention is the use of compounds which inhibit the activity of an IL-2R by contacting the IL-2R with an amount of the selected antagonist peptide sufficient to inhibit binding of IL-2 to the IL-2R under conditions that allow binding of the peptide to the IL-2R to occur.

Another object of the invention is to provide a method for the selection of antibodies specific for the purified peptide with IL-2-like activity as defined herein. These monoclonal or polyclonal antibodies can inhibit binding of IL-2 to the IL-2R under conditions that allow binding of the peptide to the IL-2R to occur. The therapeutic use of these antibodies is also a part of the present invention. In particular, these antibodies specific for the purified peptides are useful for treating or preventing undesirable immune reactions such as graft rejection or autoimmune disorders, for example, rheumatoid arthritis.

A still further object of the invention is to provide a method for inducing in a patient the biological effects of IL-2 by administering to the patient an amount of the agonist peptide of the invention sufficient to induce those biological effects, or by administering a combination of various cytokines and purified peptide. By various cytokines is meant for example IL-4, IL-9, IL-15 or IL-2.

Another object of the invention relates to the nucleic acid sequences corresponding to the amino acid sequence of the purified peptide and its derivatives according to the invention. A preferred embodiment is the nucleotide sequence encoding the purified peptide IP130 having the following sequence (SED ID NO:2):

Met Ala Pro Thr Ser Ser Ser Thr Lys Lys Thr Gln Leu Gln Leu Glu His Leu Leu Leu Asp Leu Gln Met Ile Leu Asn Gly Ile Asn Asn

This sequence or a sequence derived therefrom can be inserted in an appropriate vector capable of expressing the product in vivo, in a bacterium or in a eukaryotic cell, particularly in yeast or a mammalian cell. These constructs are useful for gene therapy among other uses.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

Various concentrations (indicated in parenthesis—μg/ml) of mAb H2-8 were tested. As control the absence of effects of mAb H2-8 on IL-2 dependent proliferation of TS1β cells was verified.

Figure 1:
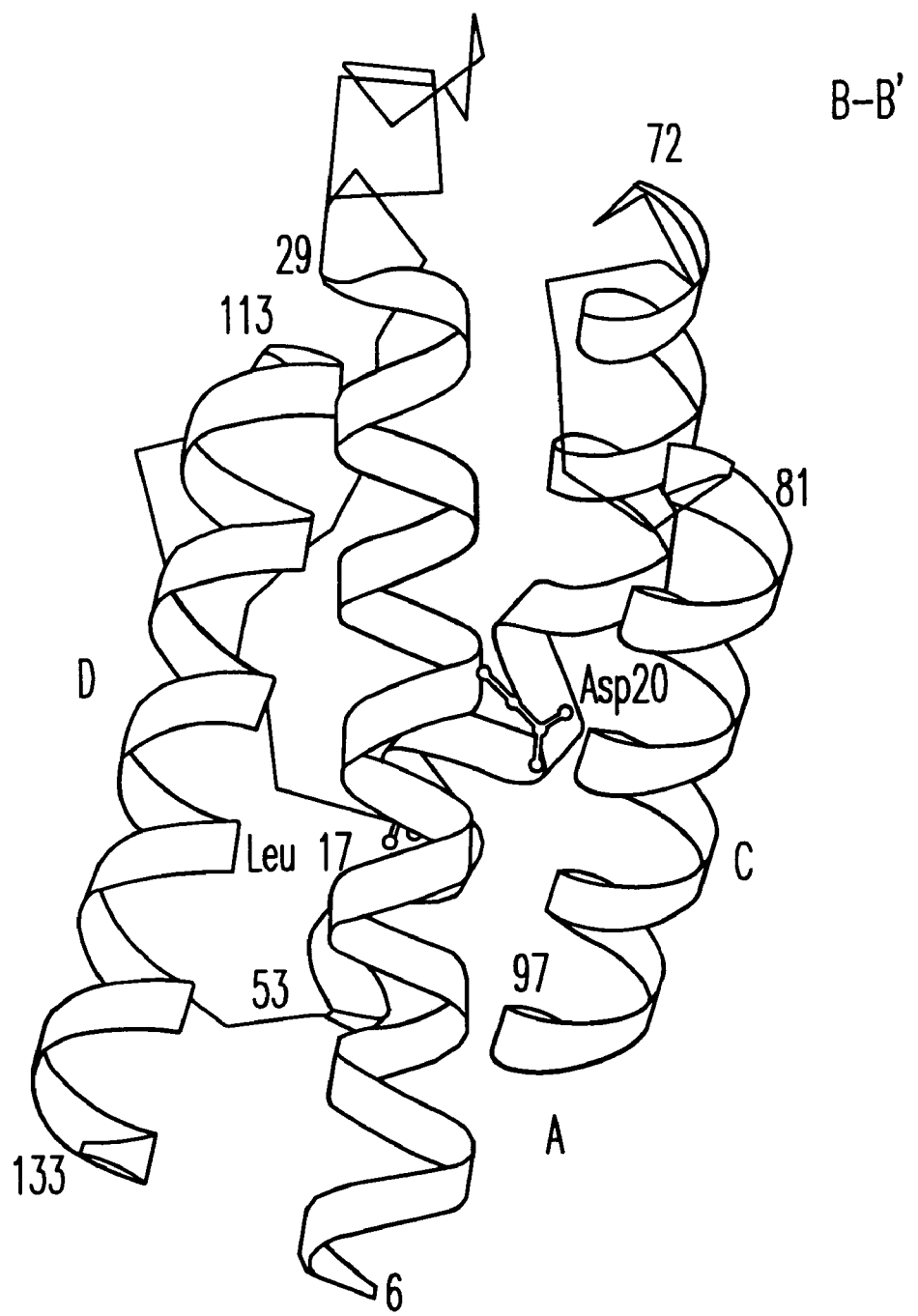
FIG. 1 shows a schematic representation of the human IL-2 structure. The protein contains 133 amino-acid residues (molecular weight: 15–18 kDa, depending on the degree of glycosylation). Four α-helices, denoted A (residue positions 6–29), B–B' (positions 53–72), C (positions 81–97), and D (positions 113–133) surround a central hydrophobic core. Residues Leu17 and Asp20 (see text) occur in the N-terminal helix A. The structure of the loop between α helix C and α helix D was undetermined. Atomic coordinates were obtained from the Brookhaven Protein Data Bank (Bernstein et al. (1977) J. Mol. Biol. 112:535–542) entry link, deposited by D. B. McKay (MacKay D (1992) Science 257:410–413). The figure was drawn with the program Molscript (Kraulis (1991) J. Appl. Crystallogr. 24:946–950).
Figure 2A:
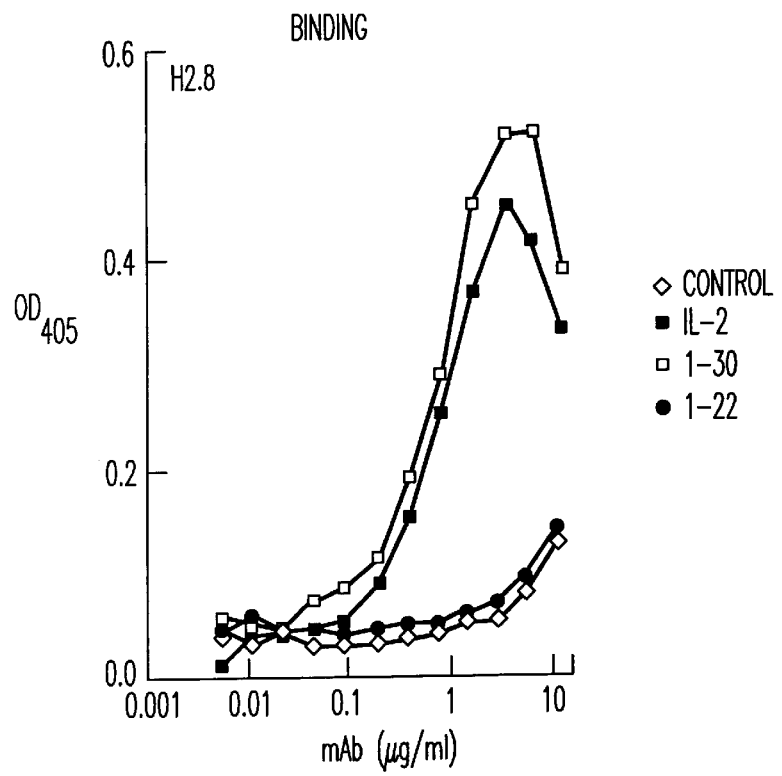
FIGS. 2A–D shows the binding and binding inhibition of mAb H2-8 which is deposited at the CNCM under the accession number I-2338 on Oct. 21, 1999. Binding experiments: plates were coated with IL-2, peptide 1-22 or peptide 1-30. Control is represented by non coated plates. Binding of mAb was revealed with alkaline phosphatase goat anti-mouse polyvalent Ig conjugate. Inhibition experiments: concentrations of mAbs H2-8 or 19B11 giving ½ maximal binding on IL-2 coated plates were used. These dilutions were mixed for 1 hr at 37° C. with the indicated concentration of inhibitors before addition to wells coated by IL-2.
Figure 2B:
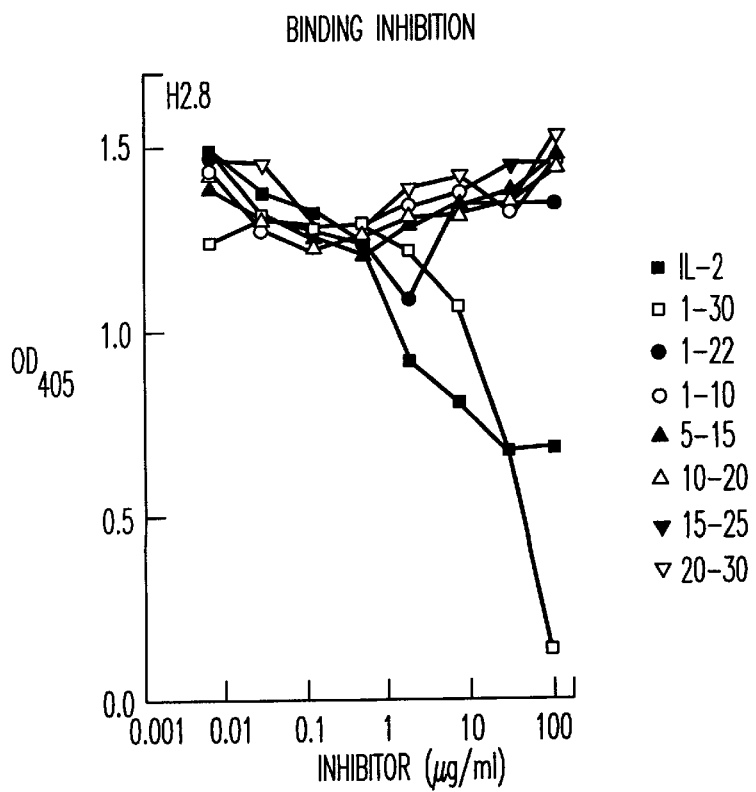
Figure 2C:
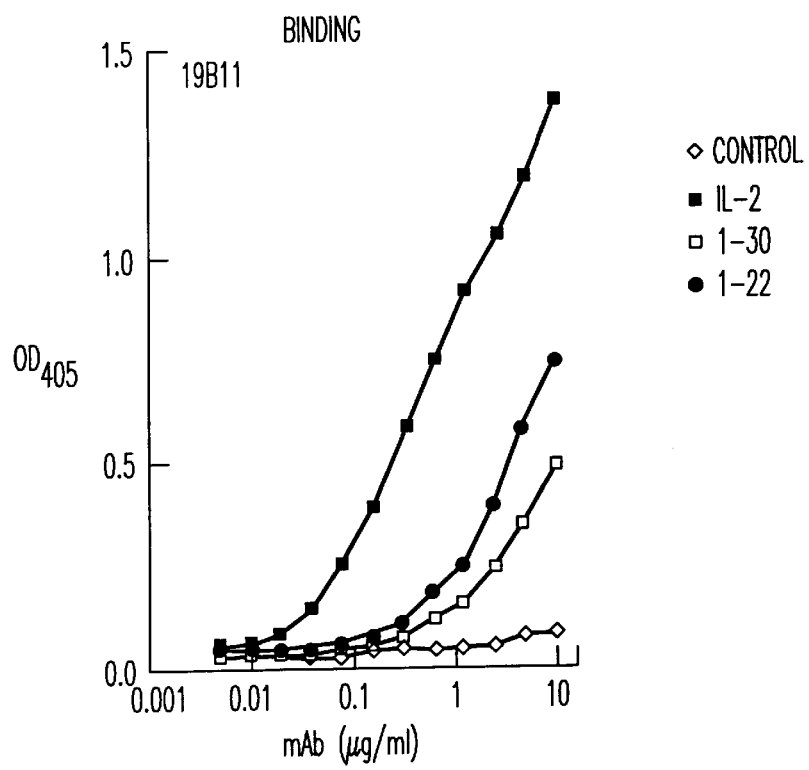
Figure 2D:
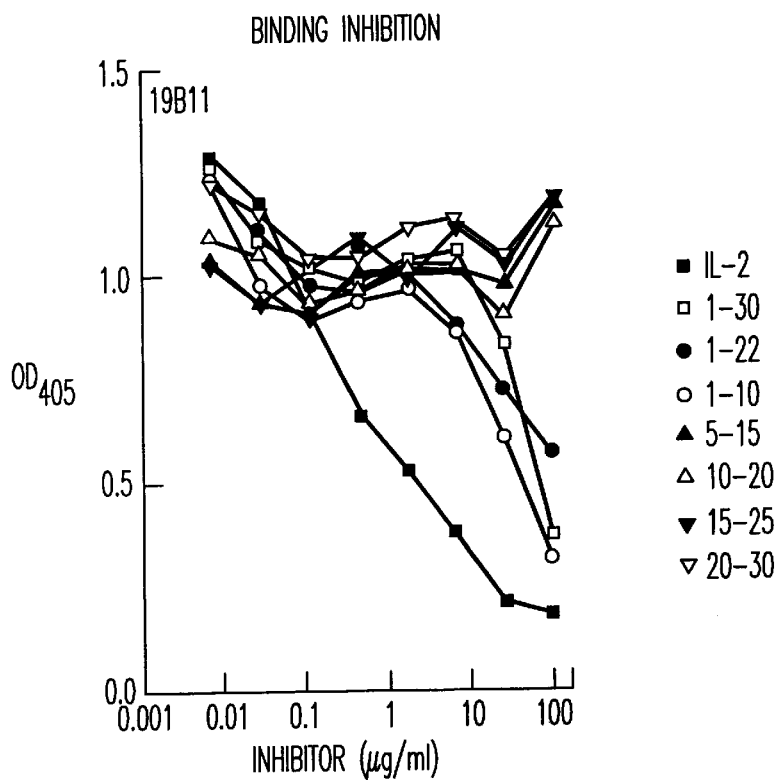
Figure 5A:
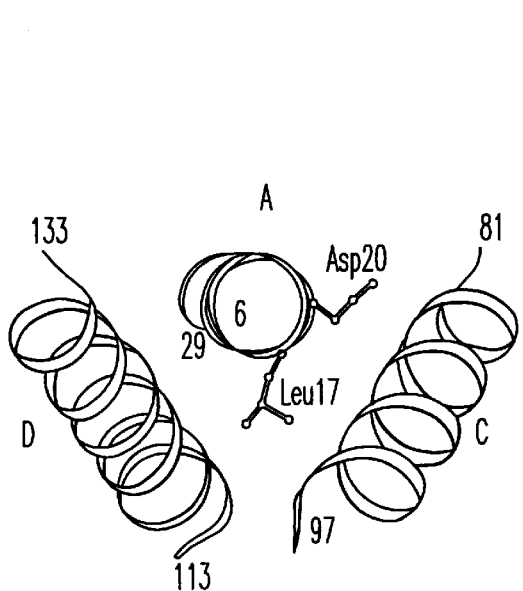
Figure 5B:
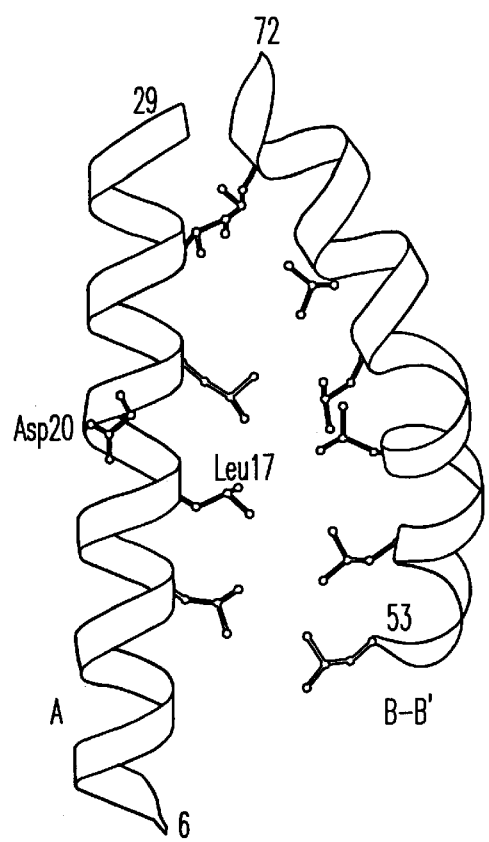
Figure 5C:
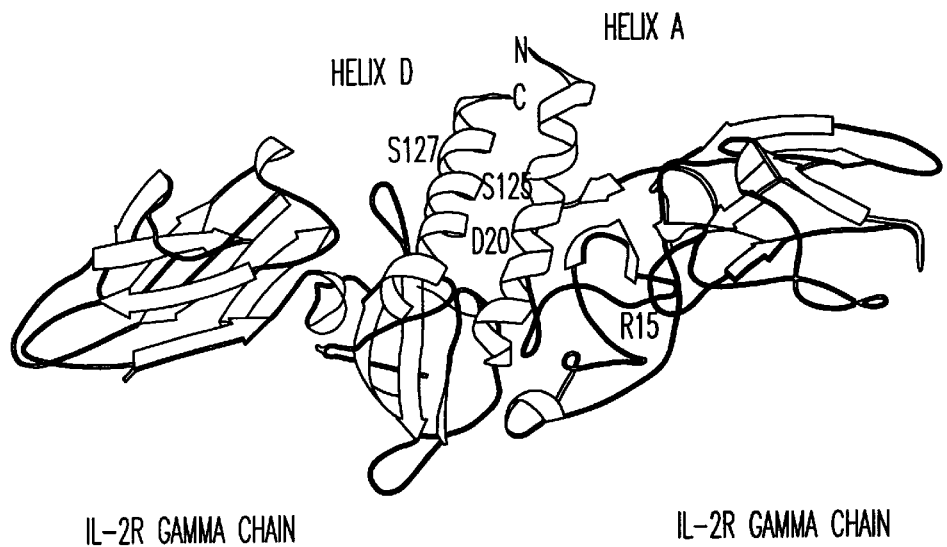
Figure 8B:
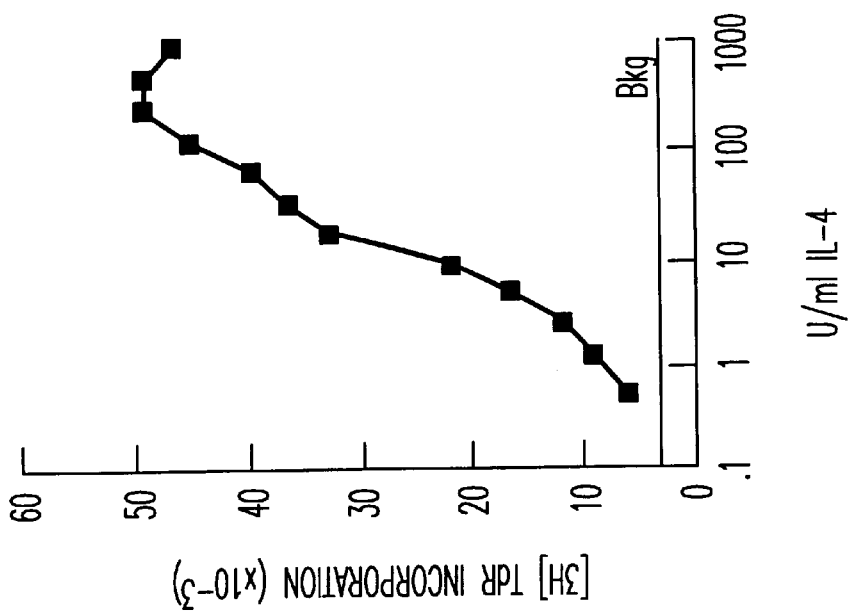
Figure 8A:
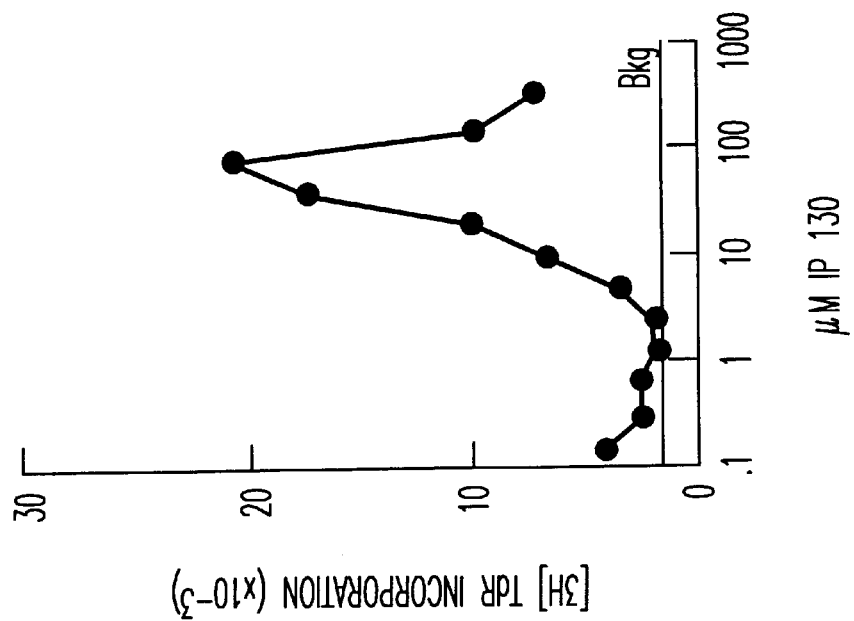
Figure 8D:
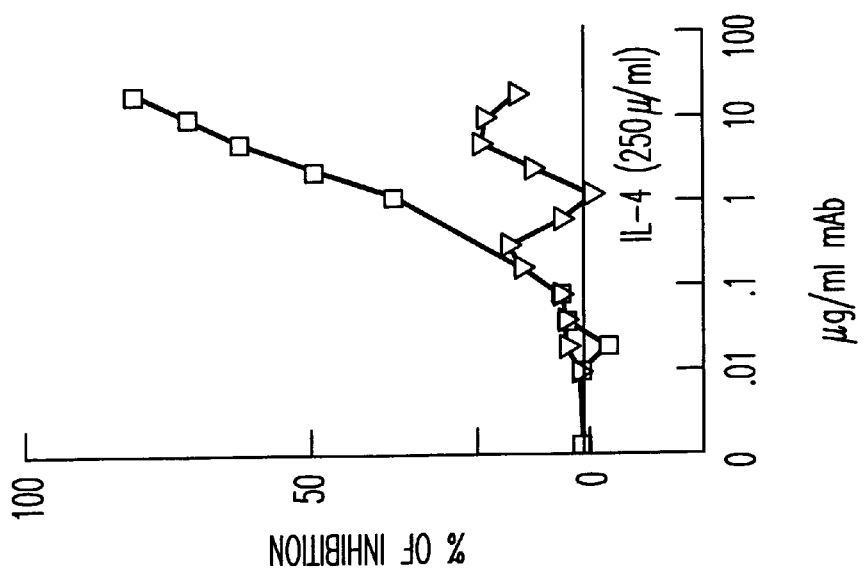
Figure 8C:
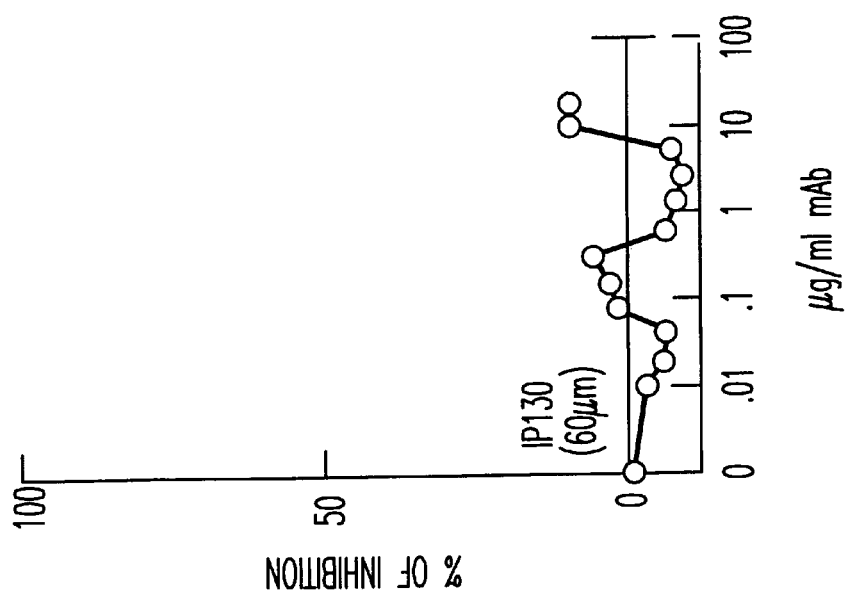
Figure 9C:
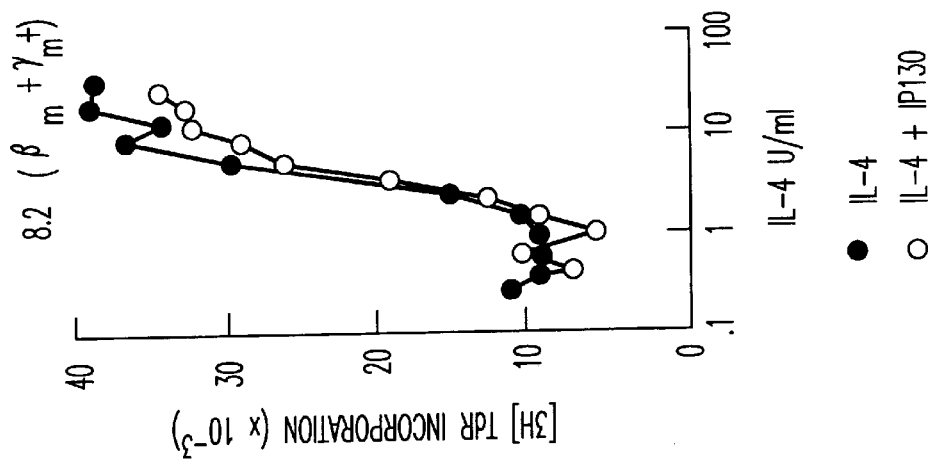
Figure 9B:
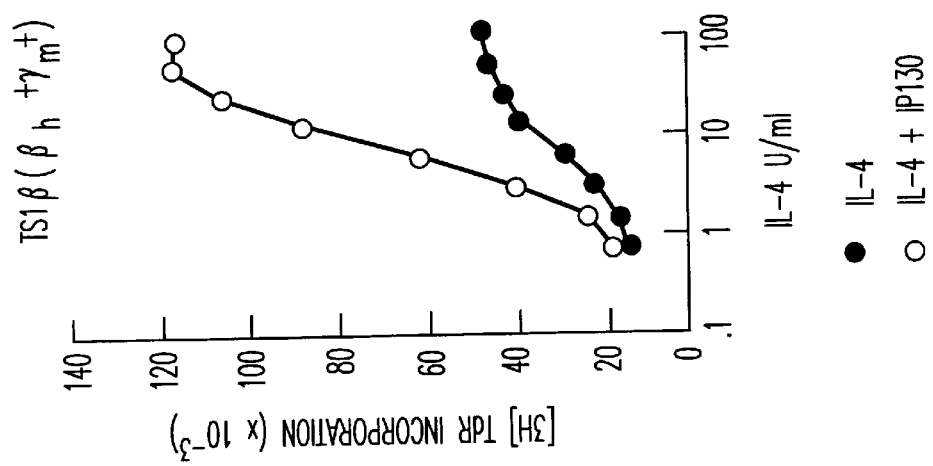
Figure 9A:
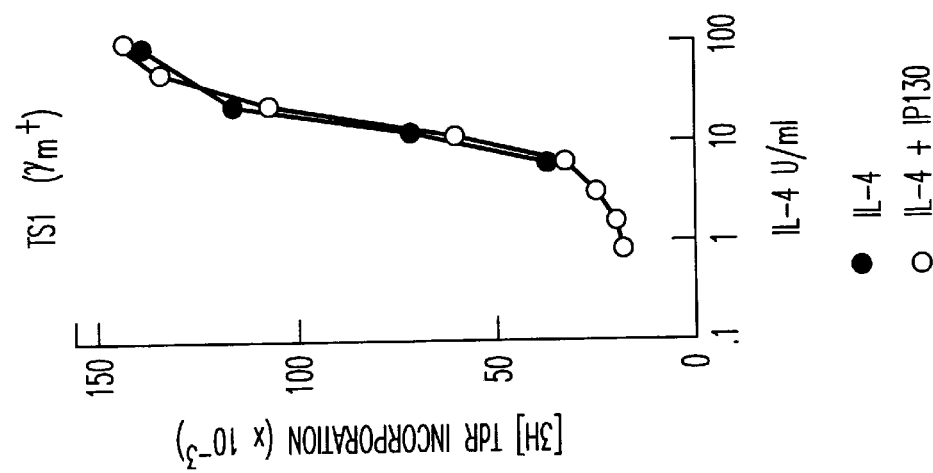

FIGS. 5A–C shows the model of IL-2/IL-2R interactions. FIG. 8(A) Position of residues Leu17 and Asp20 in the IL-2 structure with respect to helices A, C and D, in a view perpendicular to the axis of helix A. FIG. 8(B) Position of residue Leu17 with respect to helices A and B–B'. The side chain of Leu17 is located in a leucine-rich hydrophobic core of the molecule. The charged side chain of Asp20 is partly exposed to solvent. The two orientations of the molecule shown here are roughly perpendicular to that shown in FIG. 1. FIG. 8(C) The model of the IL-2/IL-2R complex (Bamborough et al. (1994) Structure 2:839–851) is based on the structure of the human growth hormone and its receptor (de Vos et al. (1992) Science 255:306–312). For clarity, only α-helices A and D of IL-2 and the β and γ chains of the receptor are shown. The IL-2 positions studied, Leu17, Asp20 and residues Arg15 and Tyr1134 of IL-2Rβ are labelled. Positions Cys125 and Ser127 are also shown. Secondary structural elements as defined by the program DSSP (Kabsch et al. (1983) Biopolymers 22:2577–2637). Atomic coordinates of the complex were obtained from the Brookhaven Protein Data Bank, entry code film.

Figure 6A:
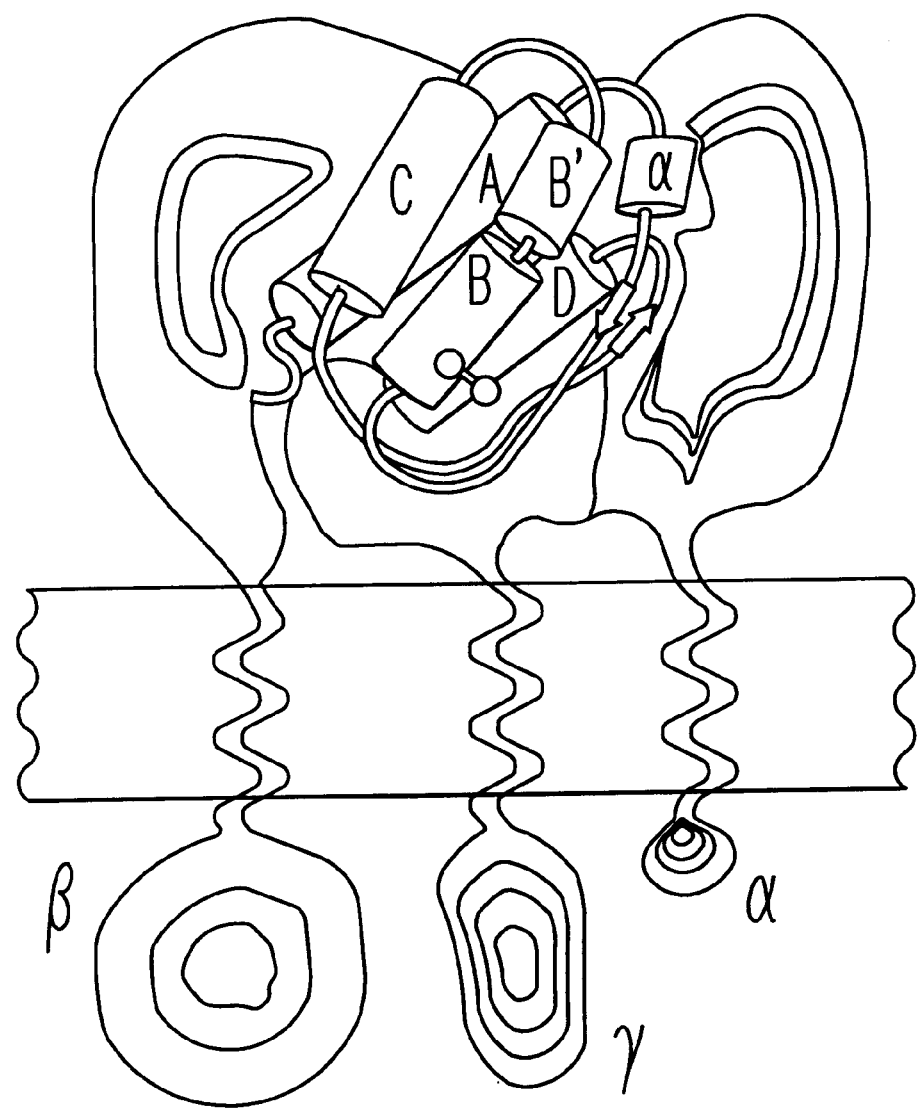
Figure 6B:
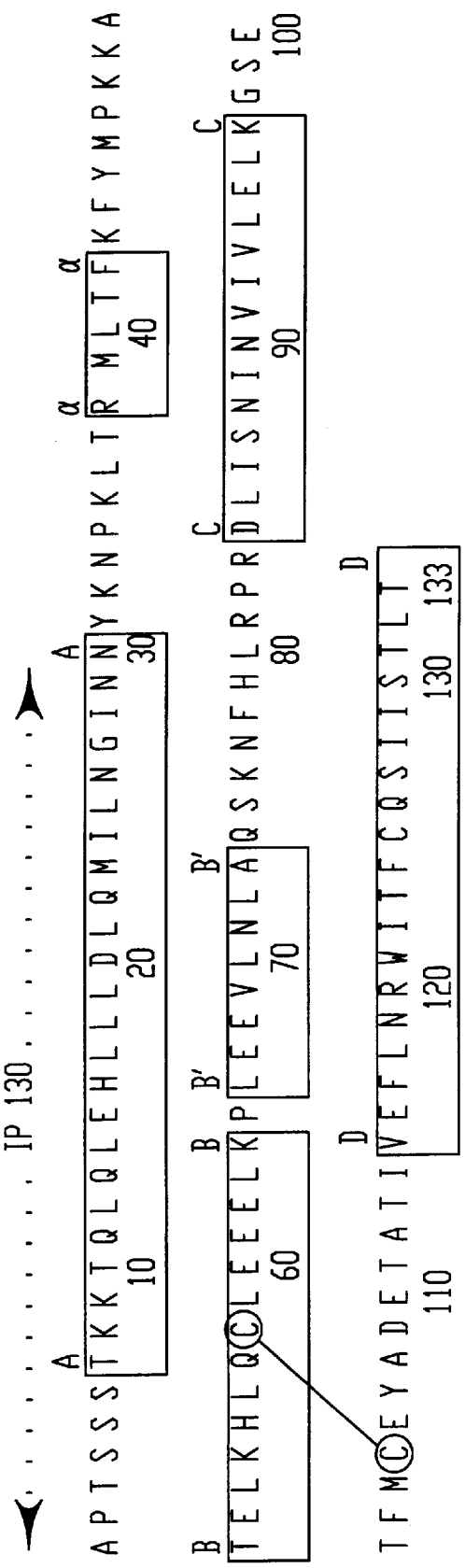

FIGS. 6A and B is a schematic representation of IL-2 (SEQ ID NO:1)/IL-2R interactions and the IP130 sequence (SEQ ID NO:2). IL-2 receptor is composed of three subunits (α, β, γ). (See Imm. Today, 1996).

Figure 7A:
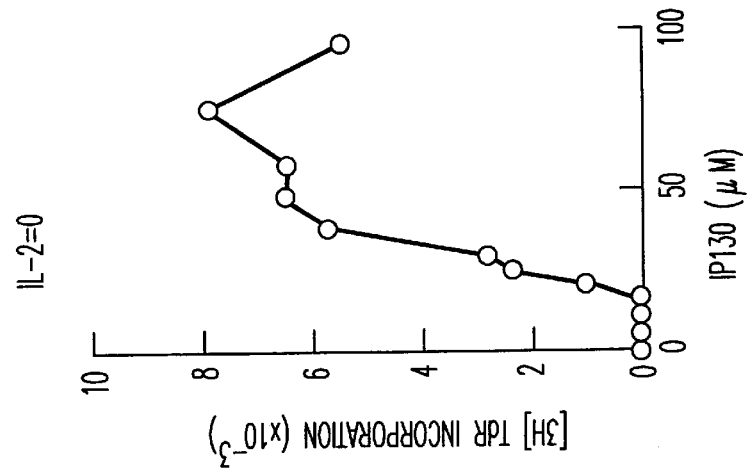
Figure 7B:
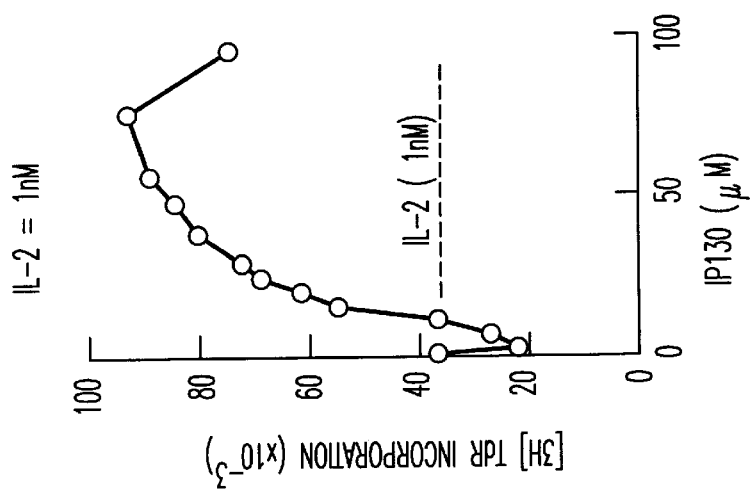
Figure 7C:
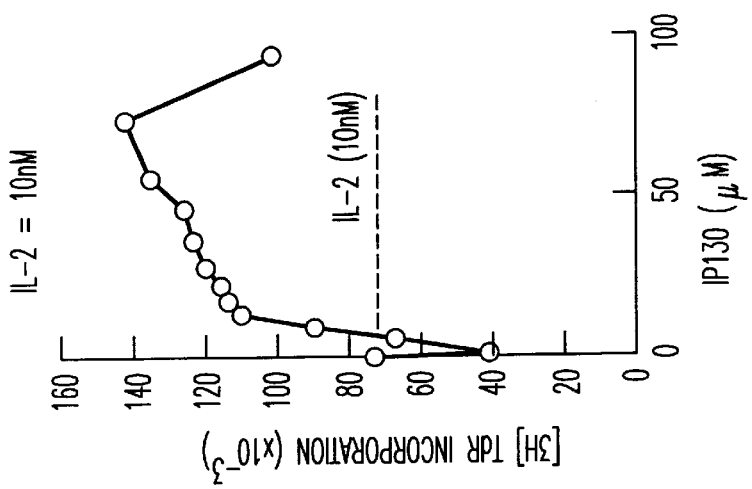

FIGS. 7A–C demonstrates that IP130 induces proliferation and acts in synergy with IL-2. Proliferative activity was tested on TS1β2 (grown in IL-2). Background of 1.4×10$^3$ cpm was subtracted. Synergy with IL-2 is also observed. TS1β target cells are derived from TS1 murine cells (which only express murine IL-2Rγ), after transfection with the human IL-2Rβ gene.

Figure 11A:
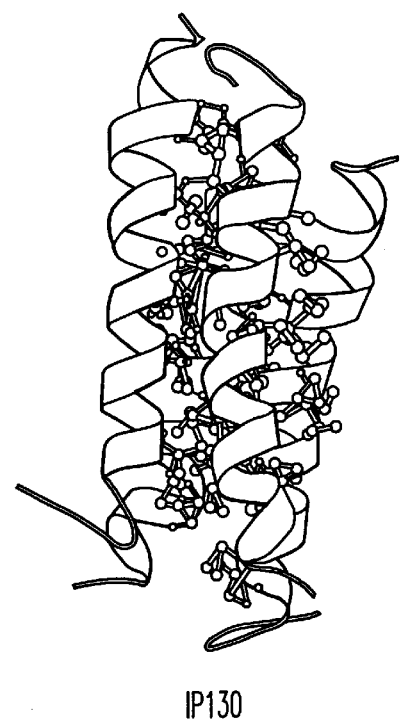
Figure 11B:
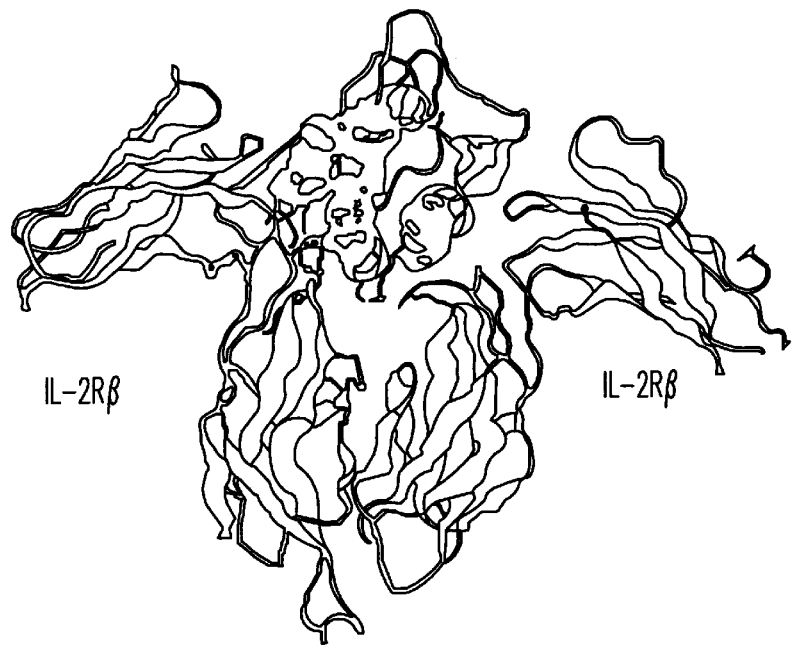

FIG. 8 shows that the proliferation induced by IP130 is not due to synergy with residual growth factor coming from the culture medium. TS1β cells, used in this study, are cultured in IL-4. TS1β proliferates with IP130 and this proliferation is not inhibited by 11B11 mAB, which neutralizes proliferation induced by IL-4. FIG. 11A shows IP130 proliferative activity. FIG. 11B shows IL-4 proliferative activity. FIG. 11C shows IP130 +mAB 11B11 (anti-IL-4). FIG. 11D shows IL-4 +mAB 11B11(□) and IL-4+mAB 145 (control mAB) (▽). Proliferative activity was tested on TS1β4 (grown in IL-4).

Figure 12A:
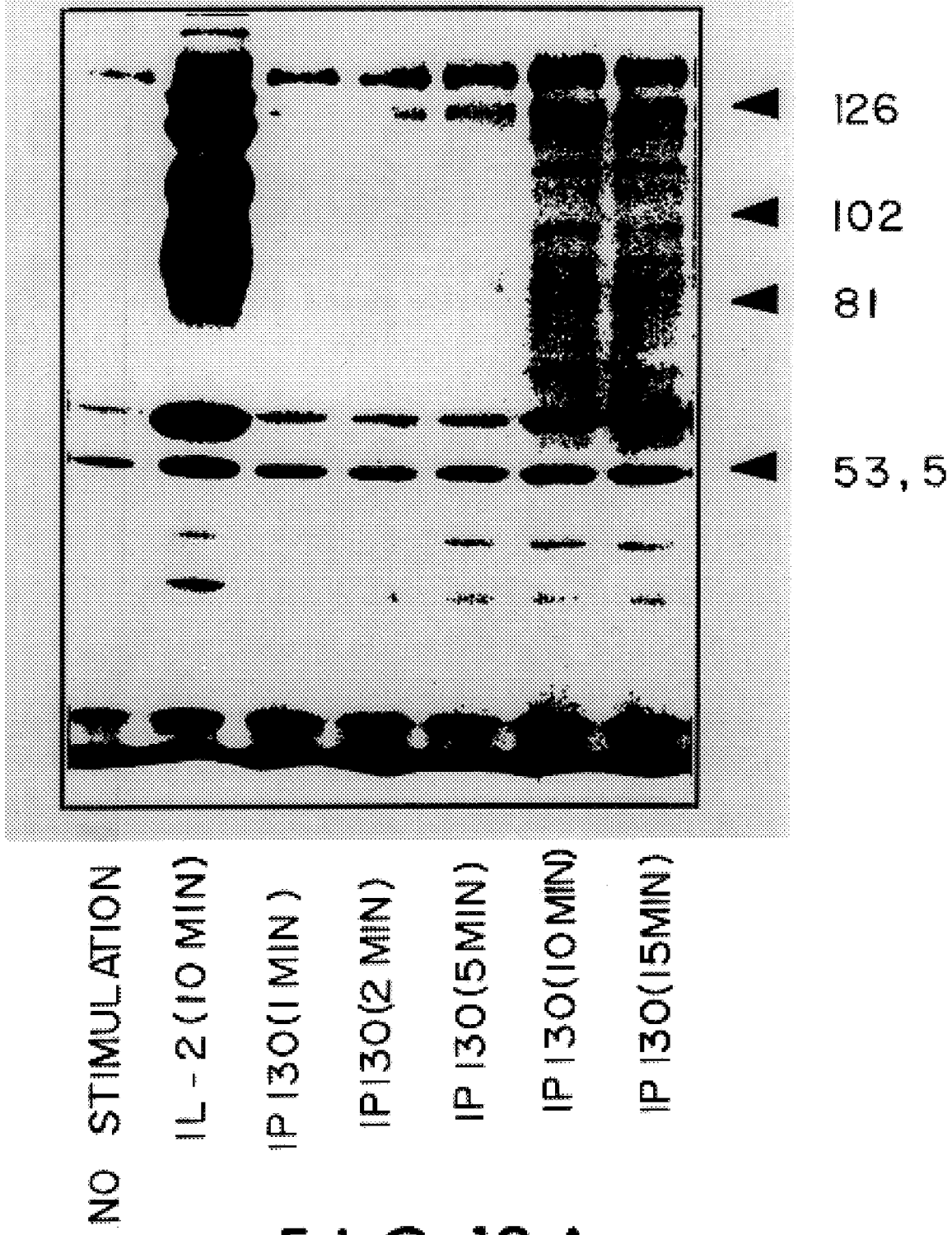
Figure 12B:
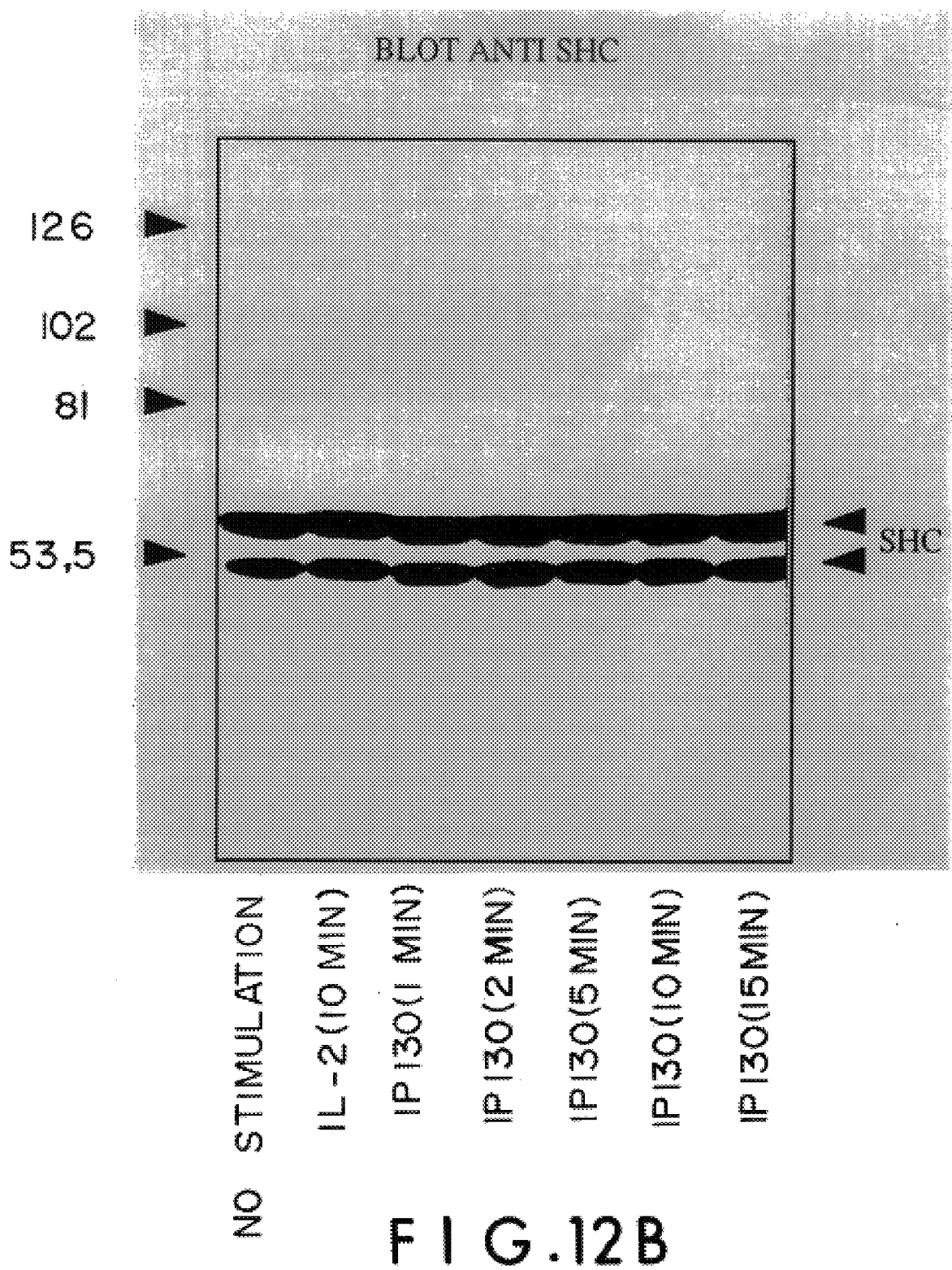

FIGS. 9A–E demonstrates that human IL-2Rβ is essential for the proliferation induced by IP130. FIGS. 12A–C shows IP130 activity on TS1 cells transfected with human IL-2Rβ. FIGS. 12D and F shows the effect of anti-human IL-2Rβ neutralizing antibody (A41) on IP130 activity. TS1 cells only proliferate after transfection by the human IL-2Rβ gene. As for IL-2, murine IL-2Rβ chain does not allow proliferation in the presence of IP130. TS1β proliferation induced by IP130 is specifically neutralized by the mAB A41 (anti human IL-2Rβ).

FIG. 10 is a summary of IP130 (SEQ ID NO:2) and of derivative molecule's structure-function studies. A family of peptides was studied for helicity, oligornerization and biologic activity (see also general presentation of the data).

FIGS. 11A and B is a model of IP130/IL-2Rβ interactions. IP130 is tetrameric and IL-2Rβ forms a dimer in solution. Proposed from the results obtained with the three dimensional structure of IL-2 and growth hormone/receptor complex.

FIG. 12 shows the pattern of phosphorylation induced by IP130 and involvement of SHC. IP130 induces SHC protein phosphorylation. The two bands corresponding to SHC isoforms are phosphorylated after a ten minute stimulation by IP130. Kinetics of Shc phosphorylation is shown on the left. A Western blot of Shc protein is shown on the right.

Figure 13:
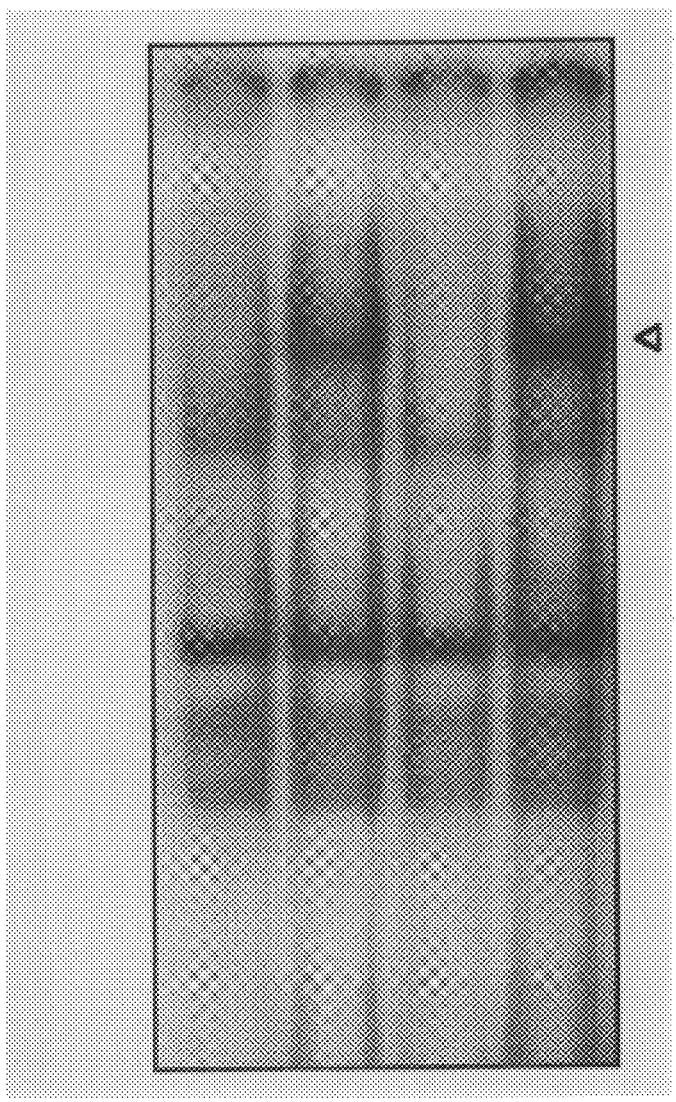

FIG. 13 is an electrophoretic mobility shift assay which shows that IP130 does not induce STAT activity. STAT activation is analyzed in KIT225 cells nuclear extracts after stimulation by IL-2, IP130 or IL-2+IP130. Only cells stimulated by IL-2 or IL-2+IP130 show a STAT activation. β-casein probes were used in the study. The same results were obtained with two other probes (GAS and GIRE).

Figure 14:
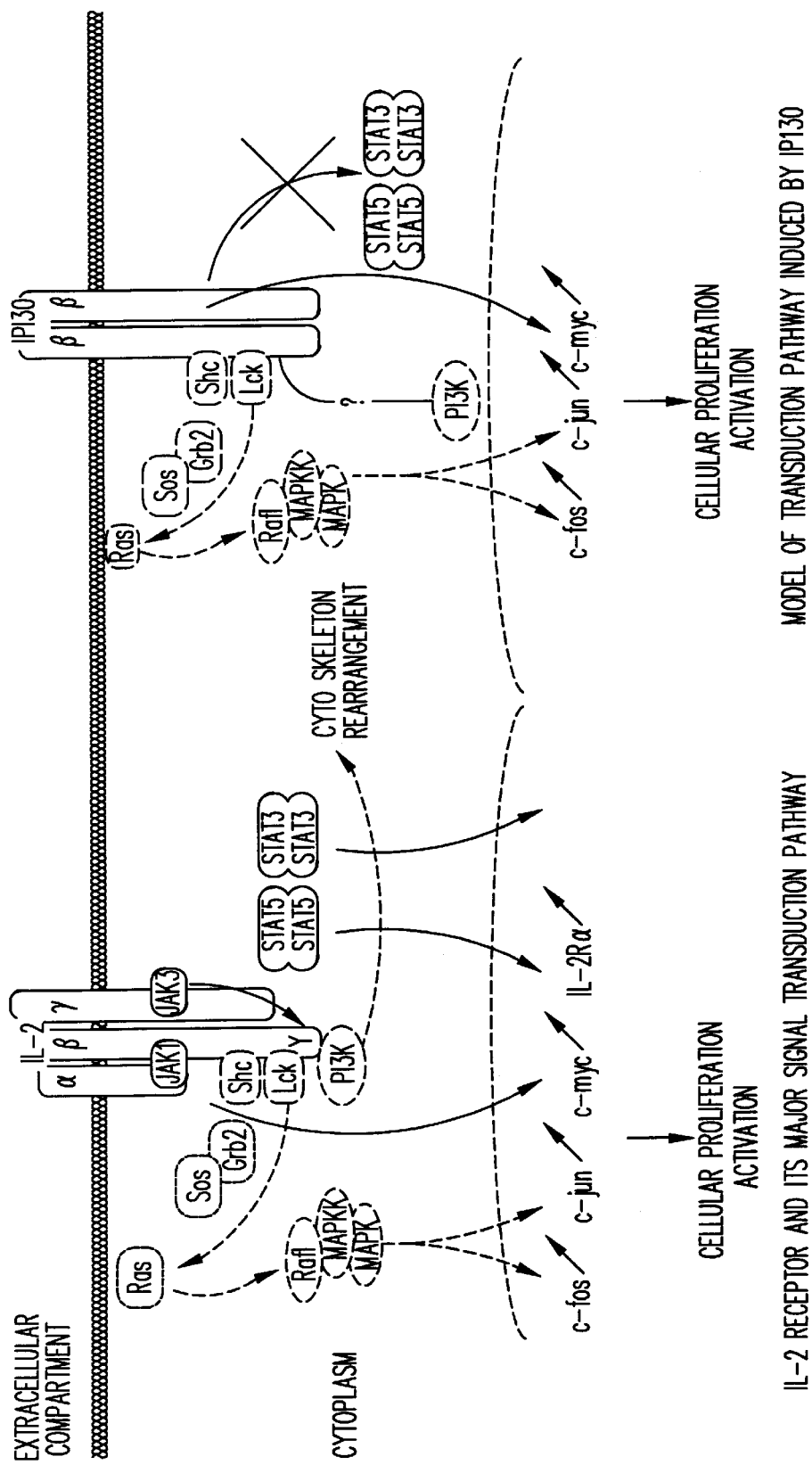
Figure 16B:
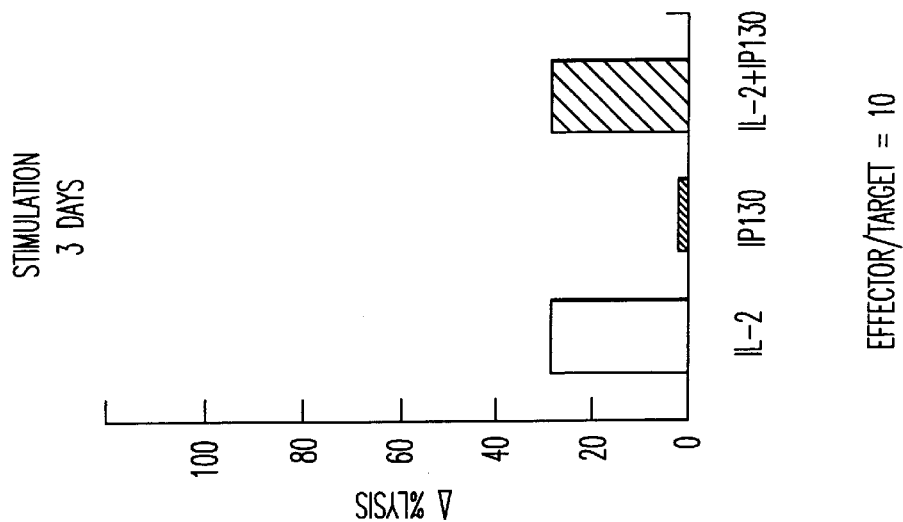
Figure 16A:
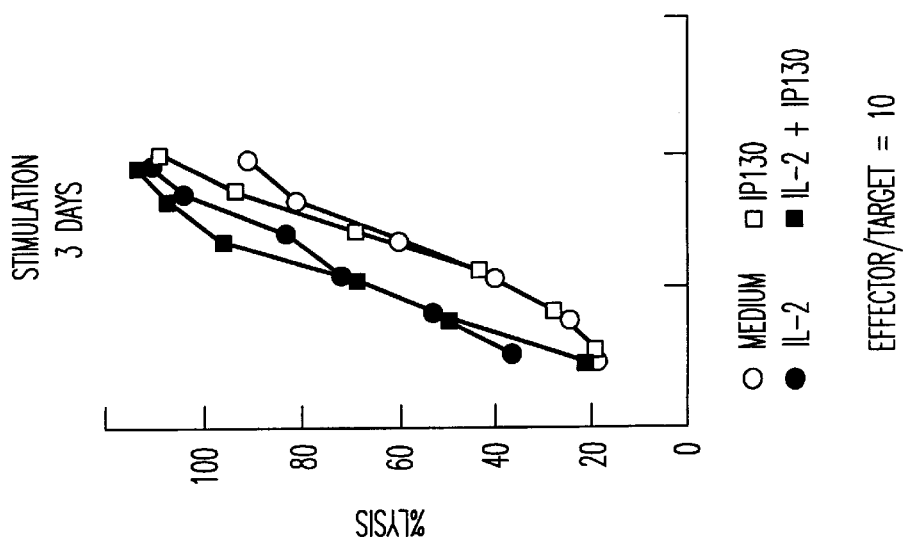
Figure 16D:
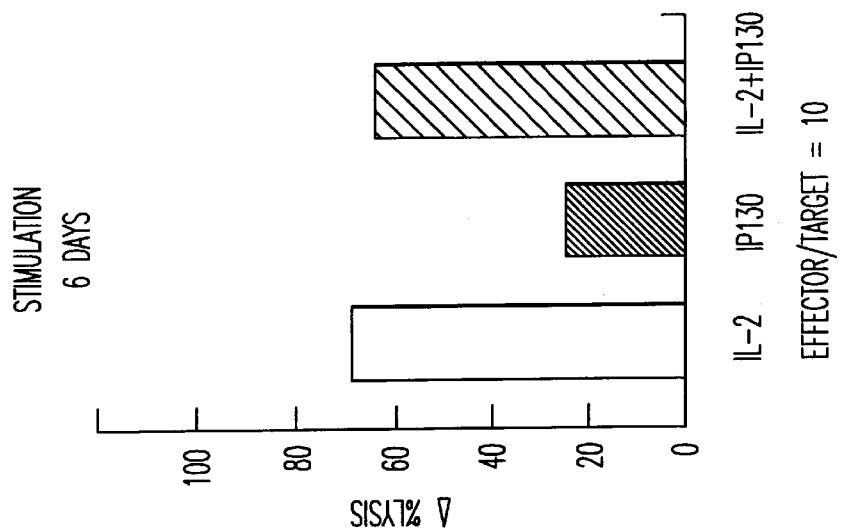
Figure 16C:
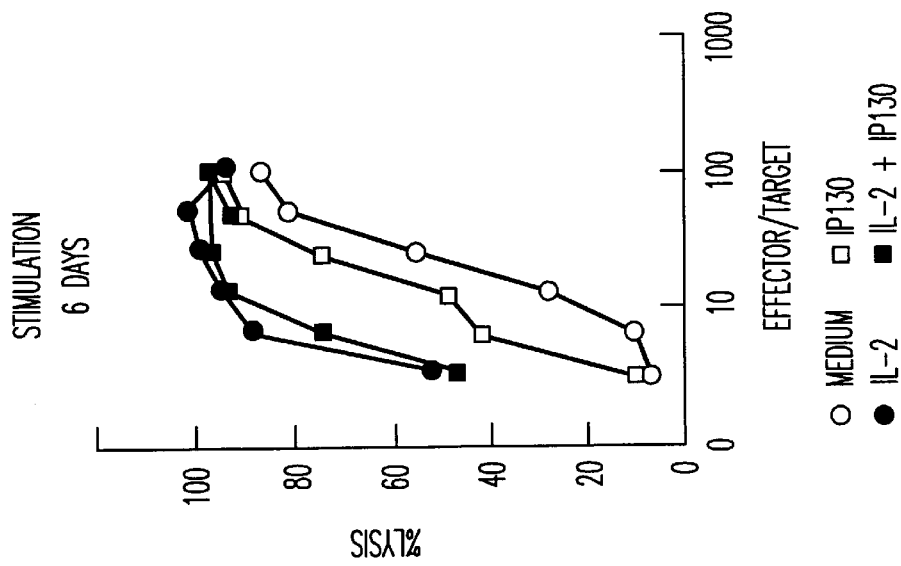
Figure 16F:
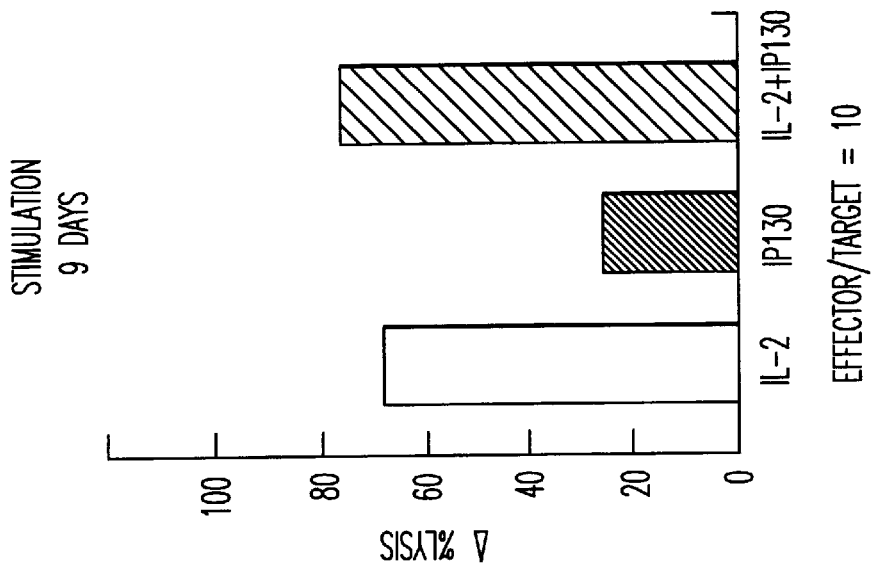
Figure 16E:
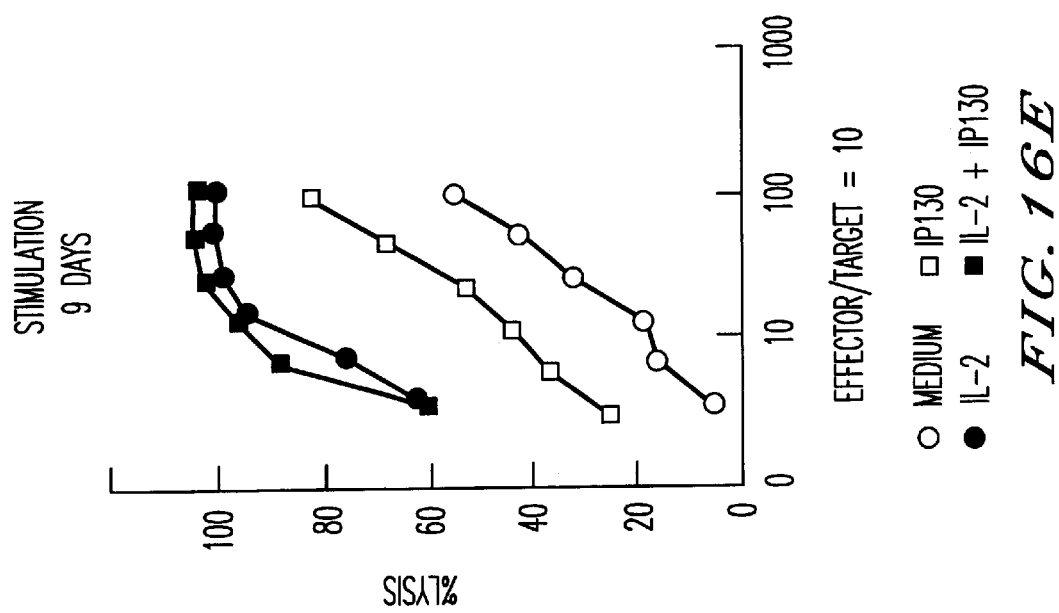

FIG. 14 depicts a model of signal transduction and IP130. IL-2 uses three main pathways: 1°/JAK/STAT depending on IL-2Rβγ complex; 2°/SHC/MAPK initiated on the phosphorylated IL-2 Rβ chain and 3°/PI3K. In accordance with the $(IP130)_4/(IL-2R\beta)_2$ model (FIG. 14), IP130 does not induce the JAK/STAT pathway but induces the SHC/MAPK pathway. (JAK: janus activated kinase; PI3K: phosphatidyl inositol, 3-phosphate kinase; STAT: signal transducers and activators of transcription; MAPKK: mitogen activated protein kinase; MAPK: mitogen activated protein kinase; ↗: induction of transcription).

FIG. 15 shows the cell cycle entry (S+G2/M) of IP130 stimulated NK cells. PBMC are stimulated by IL-2, IP130 or IL-2+IP130. Non-specific responses (J+1 in medium) are subtracted. NK cells entry into S+G2/M phases are measured by propidium iodide and analyzed with the ModFit 2.0 software (Becton Dickinson).

FIGS. 16A–F shows that IP130 stimulates LAK activity. In this experiment, the kinetics of LAK activity stimulation has been studied. Histograms show the results with an effector/target ratio of ten. Δ% lysis=lysis induced by IL-2 and/or IP130-spontaneous lysis.

DESCRIPTION OF THE PREFERRED EMBODIMENTS

The present invention relates to the use of IL-2 peptides derived from interleukin-2 (IL-2), for their therapeutic use in mammals, and particularly in humans. The peptides are selected trom fragments of IL-2 and derivatives of IL-2. The derivatives are defined as containing an amino acid sequence capable of binding to the IL-2Rβ chain under the conditions described herein, or capable of binding to the monoclonal antibodies produced by H2-8 hybridoma. The invention also relates to antibodies directed against the peptides according to the invention which likewise mimic and/or modulate IL-2 activity. The diagnostic and therapeutic approaches involve the use of the purified peptides and the antibodies for detecting and/or modulating IL-2 binding to IL-2R in vitro and in vivo.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology; A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "IL-2 peptide," "IL-2 agonist/antagonist," "IP130/IP130 derivatives," and any variants not specifically listed, may be used herein interchangeably, and as used throughout the present application. These terms refer to proteinaceous material including single or multiple proteins or recombinant product or peptides obtained by chemical synthesis, and extend to those proteins having the amino acid sequence data described herein and presented in FIG. 9 (SEQ ID NO: 1). The profile of biological activities set forth hereinafter is one of the aspects of the present application. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "IL-2 peptide," "IL-2 agonist/antagonist" and "IP130/IP130 derivatives or purified peptide (s)" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property or immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," is defined as a molecule comprised of two or more ribonucleotides, preferably more than three. Its exact size will depend upon many factors which, in turn, depend upon the ultimate function and use of the oligonucleotide.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under. for example, stringent conditions as defined for that particular system. Defining appropriate hybridization conditions is within the skill of the art. See, e.g., Maniatis et al., supra, DNA Cloning, Vols. I & II, supra; Nucleic Acid Hybridization, supra.

It should be appreciated that also within the scope of the present invention are the biological uses of the DNA sequences encoding IL-2 peptides having the same amino acid sequence as IP130 (SEQ ID NO:2), but which are degenerate to the DNA encoding SEQ ID NO:2. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Modifications of the peptides can be made in the DNA encoding SEQ ID NO:2 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups
  Alanine
  Valine
  Leucine
  Isoleucinie
  Proline
  Phenylalanine
  Tryptophan
  Methionine
Amino Acids with Uncharged Polar R Groups
  Glycine
  Serine
  Threonine
  Cysteine
  Tyrosine
  Asparagine
  Glutamine
Amino Acids with Charged Polar R Groups (negatively charged at Ph 6.0)
  Aspartic acid
  Glutamic acid
Basic Amino Acids (positively charged at pH 6.0)
  Lysine
  Arginine
  Histidine (at pH 6.0)

Another grouping may be those amino acids with phenyl groups:
  Phenylalanine
  Tryptophan
  Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced in IL-2 or peptides thereof to substitute an amino acid with a particularly preferable property. For example, a Cys may be introduced a potential site for disulflde bridges with another Cys. A Ilis may be introduced as a particularly "catalytic" site (i.e., His can act as an acid or base and is the most common amino acid in biochemical catalysis). Pro may be introduced because of its particularly planar structure, which induces β-turns in the protein's structure.

The biologically active peptides of the invention preferably encompass a region of the IL-2 sequence which includes amino acids 17–20, although one or more of these amino acid residues may be substituted with another amino acid, or a modified amino acid. The use of the preferred peptide containing at least 5 amino acids in length, more preferably 8–12 amino acids, and most preferably at least 15 amino acids in length is one aspect of the invention, as well as the use of the peptide of the invention based on amino acids 1–30 of IL-2.

Biological or physiological activity of IL-2 may be considered to include the stimulation of CD4, CD8 and NK cells, and may include antiviral and antitumor activities. Biological or physiological activity of IP 130and other peptides of the invention may include the foregoing activities of IL-2, as well as induction of SHC phosphorylation and induction of the SHC/MAPK pathway.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns. or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

Preferred antibodies of the present invention bind to the peptides of the invention, described above. The antibodies which bind the peptides of the invention may be used as diagnostic agents for analyzing IL-2 binding to its receptor, and may also be used as therapeutic agents, to enhance or inhibit the binding of IL-2 to its receptor. In a preferred embodiment, the antibody of the invention inhibits the binding of IL-2 and/or IP130 to the IL-2R.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in a feature of pathology such as for example, elevated blood pressure, fever or white cell count as may attend its presence and activity.

A DNA sequence is "operatively linlked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In its primary aspect, the present invention concerns the use of IL-2 peptides which modulate IL-2 activity. By "modulate" is meant either agonist or antagonist activity which either increases or suppresses the physiological effects of IL-2, such as the proliferation of cells, as described below.

As stated above, the present invention also relates to a recombinant DNA molecule or cloned gene, or a degenerate variant thereof, which encodes an IL-2 peptide, or a fragment thereof, that possesses a molecular weight preferably of about 2–5 kD and an amino acid sequence set forth in FIG. 9 (SEQ ID NO:2) or a sequence wherein SEQ ID NO:2 is modified by insertion, deletion and/or substitution; preferably a nucleic acid molecule, in particular a recombinant DNA molecule or cloned ,ene, encoding the peptide has a nucleotide sequence, is complementary to, or hybridizes under standard hybridization conditions to a DNA sequence encoding SEQ ID NO:2.

The possibilities both diagnostic and therapeutic that are raised by the existence of the IL-2 peptides, derive from the fact that the peptides appear to participate in direct and causal protein-protein interaction between the IL-2 peptide and the IL-2 receptor, specifically IL-2Rβ, and those factors that thereafter mediate cellular events. In particular the IP130 peptide has been shown to induce phosphorylation of IL-2Rβ, to induce c-myc; and to induce natural killer (NK) cells to enter the cell cycle. As suggested earlier and elaborated further on herein. the present invention contemplates pharmaceutical intervention in the cascade of reactions in which the IL-2R is implicated, to modulate the activity initiated by IL-2 and peptides thereof.

Thus, in instances where it is desired to reduce or inhibit the IL-2 induced activity, an appropriate IL-2 peptide inhibitor of IL-2 could be introduced to block the interaction of the IL-2 with the IL-2R. Correspondingly, instances where insufficient IL-2 induced activity is taking place could be remedied by the introduction of additional quantities of the appropriate IL-2 peptide agonist, such as IP130, or its chemical or pharmaceutical cognates, analogs, fragments and the like.

As discussed earlier, the IL-2 peptides or their binding partners or other ligands or agents exhibiting either mimicry or antagonism to IL-2 or control over its production, may be prepared in pharmaceutical compositions, with a suitable carrier and at a strength effective for administration by various means to a patient experiencing an adverse medical condition associated with undesirable levels of IL-2 for the treatment thereof. A variety of administrative techniques may be utilized, among them parenteral techniques such as subcutaneous, intravenous and intraperitoneal injections, catheterizations and the like. Average quantities of the IL-2 peptides or their subunits may vary and in particular should be based upon the recommendations and prescription of a qualified physician or veterinarian.

Also, antibodies including both polyclonal and monoclonal antibodies, and drugs that modulate the production or activity of IL-2 and/or peptides thereof may possess certain diagnostic applications and may for example, be utilized for the purpose of detecting and/or measuring IL-2 receptor activity or the like. For example, IL-2 or peptides thereof may be used to produce both polyclonal and monoclonal antibodies to themselves in a variety of cellular media, by known techniques such as the hybridoma technique utilizing, for example fused mouse spleen lymphocytes and myeloma cells. Likewise, small molecules that mimic or antagonize the activity(ies) of the IL-2 peptides of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4.399,121; 4,427,783; 4,444,887; 4,451,570; 4,466,917; 4,472,500; 4,491,632; 4,493,890.

Panels of monoclonal antibodies produced against IL-2 peptides can be screened for various properties; i.e., isotype, epitope, affinity, etc. Of particular interest are monoclonal antibodies that modulate the activity of IL-2 or peptides thereof. Such monoclonals can be readily identified in cellular proliferation assays. High affinity antibodies are also useful when immunoaffinity purification of native or recombinant IL-2 or IL-2 peptides is possible.

Preferably, the anti-IL-2 antibody used in the diagnostic methods of this invention is an affinity purified polyclonal antibody. More preferably, the antibody is a monoclonal antibody (mAb). In addition, it is preferable for the anti-IL-2 antibody molecules used herein be in the form of Fab, Fab', F(ab')$_2$ or F(v) portions of whole antibody molecules.

A diagnostic method of the present invention comprises examining a cellular sample or medium by means of an assay including an effective amount of a labeled IL-2 peptide or an antagonist thereof, such as an anti-IP130 antibody, preferably an affinity-purified polyclonal antibody, and more preferably a mAb. In addition, it is preferable for the anti-IL-2 antibody molecules used herein be in the form of Fab, Fab', F(ab')$_2$ or F(v) portions or whole antibody molecules. As previously discussed, patients capable of benefitting from this method include those suffering from cancer, a pre-cancerous lesion, a viral infection or other like pathological derangement. Methods for isolating the IL-2 peptide and inducing anti-IL-2 antibodies and for determining and optimizing the ability of anti-IL-2 antibodies to assist in the examination of the target cells are all well-known in the art.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of usefuil antibody molecules, can be prepared using, the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an IL-2 peptide or IL-2 R-binding portion thereof.

Splenocytes are typically flused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present IL-2 mutant or peptide and their ability to inhibit specified IL-2 activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM, Dulbecco et al., Virol. 8:396 (1959)) supplemented with 4.5 gm/l glucose, 20 mm glutamine, and 20% fetal calf serum. An exemplary inbred mouse strain is the Balb/c.

Methods for producing monoclonal anti-IL-2 antibodies are also well-known in the art. See Niman et al., *Proc. Nalt. Acad. Sci. USA*, 80:4949–4953 (1983). Typically, the present IL-2 peptide or a peptide analog is used either alone or conjugated to an immunogenic carrier, as the immunogen in the before described procedure for producing anti-IL-2 monoclonal antibodies. The hybridomas are screened for the ability to produce an antibody that immunoreacts with the IL-2 mutant or peptide analog.

The present invention further contemplates the use of therapeutic compositions which are useful in practicing the therapeutic methods of this invention. In one embodiment, the therapeutic composition includes, in admixture, a pharmaceutically acceptable excipient (carrier) and one or more of a IL-2 peptide, a purified peptide or a derivative thereof or a polypeptide analog thereof or fragment thereof, as described herein as an active ingredient. In a preferred embodiment, the therapeutic composition comprises an active compound containing a purified peptide capable of modulating the specific binding of the present IL-2 with the IL-2R.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol. ethanol, or the like and combinations thereof. In addition, if desired, the composition can contain minor amounts of auxiliary substances such as wetting or emulsifying agents, pH buffering agents which enhance the effectiveness of the active ingredient.

The use of the compositions may be by administration in a manner compatible with the dosage formulation, and in a therapeutically effective amount. The quantity to be administered depends on the subject to be treated, capacity of the subject's immune system to utilize the active ingredient, and degree of modulation of IL-2 binding capacity desired. Precise amounts of active ingredient required to be administered depend on the judgement of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The use of the therapeutic compositions may be by administration in a composition which further includes an effective amount of the IL-2 agonist/antagonist or analog thereof, and one or more of the following active ingredients: an antibiotic, a steroid.

As used herein, "pg" means picogram, "ng" means nanogram, "ug" or "µg" mean microgram, "mg" means milligram, "ul" or "µl" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences.

Suitable vectors include derivatives of SV40 and known bacterial plasmids, e.g., $E.$ $coil$ plasmids col E1, pCR1, pBR322, pMB9 and their derivatives, plasmids such as RP4; phage DNAS, e.g., the numerous derivatives of phage $\lambda$, e.g., NM989, and other phage DNA, e.g., M13 and filamentous single stranded phage DNA; yeast plasmids such as the $2\,\mu$ plasmid or derivatives thereof; vectors useful in eukaryotic cells, such as vectors useftil in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system. the major operator and promoter regions of phage $\lambda$, the control regions of fd coat protein, the promoter for 3-phosphoglycerate kinase or other glycolytic enzymes, the promoters of acid phosphatase (e.g., Pho5), the promoters of the yeast $\alpha$-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of $E.$ $coli$, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability. and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that for the therapeutic use of the peptides according to the invention, the IL-2 peptide analogs may be prepared from nucleotide sequences of the protein complex/subunit derived within the scope of the present invention. Analogs, such as fragments, may be produced, for example, by pepsin digestion of IL-2 material. Other analogs, such as muteins, can be produced by standard site-directed mutagenesis of IL-2 coding sequences. Analogs exhibiting "IL-2 activity" such as small molecules, whether functioning as promoters or inhibitors, may be identified by known in vivo and/or in vitro assays.

As mentioned above, a DNA sequence encoding IL-2 peptides can be prepared synthetically rather than cloned. The DNA sequence can be designed with the appropriate codons for the IL-2 peptide amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express IL-2 peptide analogs or "muteins". Alternatively, DNA encoding muteins can be made by site-directed mutagenesis of native IL-2 genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

In accordance with the gene therapy applications of the present invention, the preparation of antisense oligonucleotides and ribozymes may be used to modulate the expression of IL-2 at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into cells. Antisense methods have been used to inhibit the expression of many genes in vitro (Marcus-Sekura, 1988; Hambor et al., 1988).

The DNA sequences described herein may thus be used to prepare antisense molecules against, and ribozymes that cleave mRNAs for IL-2 or molecules which stimulate or reduce IL-2 secretion and their ligands.

The present invention also relates to a variety of diagnostic applications, including methods for detecting IL-2 presence and activity, by reference to their ability to elicit the activities which are mediated by the present IL-2 peptides. As mentioned earlier, the IL-2 peptide can be used to produce antibodies to itself by a variety of known techniques, and such antibodies could then be isolated and utilized as in tests for the presence of particular IL-2 and/or IL-2R activity in suspect target cells.

As described in detail above, antibody(ies) to the IL-2 peptides can be produced and isolated by standard methods including the well known hybridoma techniques. For convenience, the antibody(ies) to the IL-2 peptide will be referred to herein as $Ab_1$ and antibody(ies) raised in another species as $Ab_2$.

The presence of IL-2 and IL-2 peptides in cells can be ascertained by the usual immunological procedures applicable to such determinations. A number of useful procedures are known. Three such procedures which are especially useful utilize either the IL-2 peptide labeled with a detectable label, antibody $Ab_1$ labeled with a detectable label, or antibody $Ab_2$ labeled with a detectable label. The procedures may be summarized by the following equations wherein the asterisk indicates that the particle is labeled, and "ILP" stands for the IL-2 peptide:

A. $ILP^* + Ab_1 = ILP^*Ab_1$

B. $ILP + Ab^* = ILPAb_1^*$

C. $ILP + Ab_1 + Ab_2^* = ILPAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the ILP forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-ILP antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The IL-2 peptide or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system which can be utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

A further embodiment of this invention is the diagnostic application of commercial test kits suitable for use by a medical specialist. The kit may be prepared to determine the presence or absence of predetermined IL-2R activity or predetermined IL-2 activity capability in suspected target cells. In accordance with the testing techniques discussed above, one class of such kits will contain at least the labeled IL-2 peptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined IL-2R activity, comprising:

(a) a predetermined amount of at least one labeled immunochemically reactive component obtained by the direct or indirect attachment of the present IL-2 peptide factor or a specific binding partner thereto, to a detectable label;

(b) other reagents; and (c) directions for use of said kit.

More specifically, the diagnostic test kit may comprise:

(a) a known amount of the IL-2 peptide as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the Il-2 peptide to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the IL-2 peptide and a specific binding partner thereto.

Having generally described this invention, a further understanding can be obtained by reference to certain specific examples which are provided herein for purposes of illustration only and are not intended to be limiting unless otherwise specified.

EXAMPLES

Example 1

Characterization of Mouse Monoclonal Antibody H2.8

Female BALB/c mice were repeatedly immunized with 25 to 50 μg of peptide 1-30 per injection. The peptide was coupled to the KLH carrier and injected with Complete Freund's adjuvant (first injection) or incomplete Freund's adjuvant (subsequent injections). The titer of the anti-IL-2 activity was assessed in a group of five animals. Spleen cells from the animal giving the best response were used for fusion with cell line SP2-0. Four hybridomas with specific anti-IL-2 activity were cloned. The mAbs were purified from the corresponding ascitic fluid by amonium sulfate precipitation. The purity of the reagents (>80%) was verified by polyacrylamide gels. The properties of the mAbs were characterized. The results are reported only for mAb H2-8. The isotype (IgG1) and the K(d $(1.4 \times 10^{-9}M)$ of mAb H2-8 were determined.

Mouse mAbs 19B11 (IgG1) and 2C4 IgG1) previously characterized (Moreau et at (1995b) Mol. Immunol. 32:1047–1056; Rebollo et al (1992) Mol. Immunol. 29:119–130) were used as controls. mAbs 19B11 and 2C4 inhibit the binding of IL-2 to IL-2Rβ and recognize the peptides 1-10 (see below), 1-22 and 1-30. Rat monoclonal 11B11 (IgG, k) specific for murine IL-4 was provided by Dr. W. Paul (National Institute of Health, Bethesda Md., USA and used as previously described (Moreau et al. (1995b) Mol. Immunol. 32:1047–1056).

The inhibitory effect of purified mAb 2–8 was first assayed on the binding of $^{125}$I-labeled IL-2. Its effects were measured on two transfectants derived from a mouse cell line expressing only mIL-2Rγ. Transfectant TS1β and TS1α were obtained after transfection with human IL-2Rβ and human IL-2Rα cDNA, respectively. Both cell lines bind IL-2. mAb H2-8 inhibits the binding of IL-2 to TS1β without significantly affecting IL-2 binding to TS1α (data not shown).

The binding properties of mAb H2-8 were studied by ELISA. Plates were coated with either IL-2 or peptides 1-22 or 1-30. mAb H2-8 binds to IL-2 and peptide 1-30, but does not recognize peptide 1-22. As control mAb 19B11 (previously characterized) recognized both peptides (FIG. 2).

Binding inhibition experiments were performed to further characterize the specificity of mAb H2-8. Plates were coated with IL-2 and a concentration of mAb H2-8 giving approximatively 50% of maximum binding was used. H2-8 was preincubated with different peptides including five decapeptides (1-10, 5-15, 10-20, 15-25, 20-30). Only IL-2 and peptide 1-30 were able to inhibit the binding of mAb H2-8 to IL-2. Peptide 1-30 was the most efficient inhibitor in these experiments (FIG. 2). This result is compatible with the fact that isolated peptide 1-30 folds in an α helical configuration (α-helix content of 50%±7%) whereas peptide 1-22 does not (13%±5%) as measured by circular dichroism. Therefore peptide 1-30 may adopt some unique structural conformation very close to that of native IL-2. As control the binding of mAb 19B11 is inhibited by IL-2 but also by peptides 1-10, 1-22 and 1-30. This confirms that the epitope of mAb 19B11 is near the $NH_2$ terminal position of IL-2 as previously suggested (Moreau et al. (1995b) Mol. Immunol. 32:1047–1056).

Example 2
Peptide Synthesis

Peptides were synthesized by the stepwise solid-phase using the Boc/trifluoroacetic acid method (Merrifield (1963) J. Am. Chem. Soc. 85:2149–2145), on a p-methyl-benzhydrylamine resin (Applied Biosystems) with an Applied Biosystems 430A peptide synthesizer.

Example 3
Involvement of aa at Positions 17 and 20 in mAb H2-8 Recognition

The reactivity of mAb H2-8 to various IL-2 mutants including one mutant at position 17 (Leu→Asp), four mutants at position 20 (Asp→Asn; Asp→Lys: Asp→Arg and Asp→Leu) and a double mutant 17–20 (Leu17→Asp and Asp20→Leu) were tested by Western blot analysis (FIG. 3).

mAb H2-8 does not recognize mutations at position 20 or the double mutant (Thèze J. (1994) Eur. Cytokine Netw. 5:353–368; Moreau et al. (1995a) J. Immunol. 155:3401–3408; Chastagner et al. (1996) Eur. J. Immunol. 26:201–206; MacKay D (1992) Science 257:410–413). Recognition of the mutation at position 17 is also affected. As positive control the results obtained with mAb 2C4 that recognize an epitope near the $NH_2$ terminal area of IL-2 are shown. Since this mAb (as 19B11) recognizes peptide 1-10 which bears no mutation, its binding to IL-2 is not affected. Similarly mutations at position 125 and/or 127 do not affect binding to mAbs H28 and 2C4, and serve as additional controls. ELISA experiments performed with all the mutants support the data obtained with Western blots (data not shown).

mAb H2-8 (deposited at CNCM as accession no. I-2338 on Oct. 21, 1999 and 19B11 (described in *Molec. Immunol.* (1995) 32:1047–1056) have similar properties: both bind to the $NH_2$ terminal end of IL-2 and specifically inhibit the binding of IL-2 to IL-2Rβ chain. Since both antibodies recognize sequences located in peptide 1-30 it was of interest to compare the relationship between the corresponding epitopes. Plates coated with mAb H2-8 were used to bind peptide 1-30. The binding of mAb 19B11 to these plates was positive, thus indicating that the epitopes of mAbs H2-8 and 19B11 do not overlap significantly. Various controls performed to verify these results are shown (FIG. 3). The binding of 19B11 is strictly dependent on the presence of peptide 1-30 and on the coating by mAb H2-8. Results obtained with mAb 3H9 recognizing the peptide 30-54 further demonstrated the specificity of the data presented in FIG. 3.

Example 4

Cell Lines, Culture Media and Proliferation Assay

TS1 cells express only mouse IL-2Rγ. TS1β cells were obtained after transfection of TS1 cells with human IL-2Rβ cDNA cloned in the pdKCR expression vector kindly provided by Dr. T. Taniguchi (Institute for Molecular and Cellular Biology, Tokyo University, Japan). TS1α cells were obtained after transfection of TS1 cells with human IL-2Rα cDNA cloned in pCMV4 expression vector provided by Drs W. A. Kuziel and W. C. Greene (Gladstone Institute Virol./Immunol., San Francisco Calif., USA). TS1β and TS1α were previously characterized (Pitton et al. (1993) Cytokine 5:362–371). CTLL2 and YT were also used for IL-2 binding studies.

All cultures were performed in complete medium composed of RPMI 1640 (BioProducts, Walkerville, Md.), 10% heat inactivated FCS (Serovial, Vogelgsun, France), 2 mM glutamine, 100 units/ml penicillin, 100 μg/ml streptomycin, 50 mM 2-β-mercaptoethanol (2βME). TS1β and TS1α cell lines were grown as TS1 cells in complete medium supplemented with supernatant of recombinant baculovirus expressing murine IL-9 proteins (DIB 349) (Uyttenhove et al. (1988) Proc. Natl. Acad. Sci. USA 85:6934–6938).

TS1β cells were cultured ($10^4$ cells/well) in 96 wells in flat-bottomed microtiter plates with a final volume of 0.2 ml. Various concentrations of human rIL-2, IL-2 muteins or mouse rIL-9 were assayed. In order to test the inhibitory effect of mAbs, different concentrations of these reagents were mixed in the culture wells with the respective lymphokines for 30 min at low temperature before adding the cells. The inhibitory effects of mutein 20 Leu (described in *Cytokine* (1997) 9:488–498, which is incorporated herein by reference in its entirety) was studied by preincubating the cells (30 min at 4° C.) with the indicated concentration of inhibitor before adding IL-2 or IL-9 to the wells. Cultures were pulsed with 0.5 μCi/well of ($^3$H) TdR after 36 h of incubation and harvested 15 h later.

Example 5

Biological Properties of mAb H2-8

The biological properties of mAb H2-8 were evaluated on the proliferation of the IL-2- or IL-9-dependent TS1β cell line (FIG. 4). In these experiments the IL-2 mutant IL-2 $Pro^{125}$ (Cys→Pro) was used. This mutation slightly reduces the affinity of IL-2 for IL-2R without affecting the maximum proliferation obtained when higher concentrations of mutant are used.

FIG. 4 shows that different concentrations of mAb H2-8 reduce the IL-2 proliferation of TS1β. A progressive shift of the IL-2 titration curve is observed with increasing concentrations of mAb H2-8. Inhibitory effects of mAb H2-8 are comparable to those obtained with mAb 19B11, which was also found to inhibit the proliferation of cells bearing high affinity IL-2R (Moreau et al. (1995b) Mol. Immunol. 32:1047–1056). Addition of both mAb H2-8 and 19B11 completely abolishes IL-2 proliferation even at a very high dose of IL-2.

As controls FIG. 4 shows that mAb 11B11 (specific for mouse IL-4) does not affect the IL-2-dependent proliferation of TS1β. IL-9-induced proliferation of TS1β is also not affected by either H2-8 or 19B11.

Example 6

IL-2 Binding Assay and Inhibition

The IL-2 binding assay was performed as already described (Moreau et al. (1995b) Mol. Immunol. 32:1047–1056). $^{125}$I-labelled IL-2 binding to different cell lines was first studied. Inhibition experiments were performed at concentration of $^{125}$I-labelled IL-2 giving between 50 to 70% maximum binding. The effects of the different muteins was analyzed after 1 hr preincubation at 4° C. followed by incubation with $^{125}$I-labelled IL-2 (3 hr at 4° C.). In each experiments non-specific binding was determined. The data were expressed as % inhibitory capacity of the different mutein versus wild type protein.

Example 7
Physico-chemical Properties of Peptide IP130 (*Cytokine*, 1997)

The amino terminal peptide of IL-2 including aa 1 to 30 has a molecular weight of 3422.

The circular dichroism studies performed with IP130 indicates that at 20° C., in phosphate buffer (20 mM, pH7.2), 50% of the residues are in an α helix configuration.

The quaternary structure of peptide IP130 was also studied by sedimentation-diffusion equilibrium. At concentration above $5 \times 10^{-6}$M, most of the molecules are in a tetrameric form (in equilibrium with an octomeric complex).

The aminoacid sequence 1 to 30 shows 7 leucines and 2 isoleucines among the first 20 residues. The periodicity of these aa as well as the above results suggest a structural model for IP130 that would comprise 4 peptides organized in 4 α helices. In this model leucines and isoleucines side chains appear on the same face. This face is hydrophobic and four of these faces would build an hydrophobic core inaccessible to water. At high concentration peptide 1-10 tend to dimerize and this would explain the formation of octameric peptides.

The binding of IP130 to soluble IL-2Rβ chain was studied. Soluble IL-2Rβ has been found to be dimeric in solution. From the results, a structural model has been proposed: the complex would include four IP130 peptides and two IL-2Rβ chains ((IP130)$_4$/(IL-2Rβ)$_2$).

Example 8
Biological Properties of IP130

Studies were performed either with a murine cell line transfected by human IL-2Rβ gene (TS1β) or with an IL-2 dependant human leukemic cell line (Kit 225 from Dr. T. Hori).

IP130 stimulates the proliferation of TS1β in the absence of IL-2. In the presence of IL-2 a strong synergy is observed with the peptide. Both activities are obtained at comparable concentrations (IC-50≈μM).

IP130 acts only on cell lines expressing human IL-2Rβ. This is in agreement with previous studies showing that murine IL-2Rβ does not bind IL-2 (Chastagner et al. 1996, Eur. J. immunol. 26:201–6). Consequently, classical murine cell lines (C30-1, CTLL, HT-2, . . . ) usually used to assay IL-2 activity remains insensitive to IP130 effects. Furthermore anti-human IL-2Rβ blocking mAb neutralizes the effects of IP130.

Alone the peptide induces the phosphorylation of proteins on Kit 225 cell line. On the pattern of phosphorylated proteins, the kinase Shc is easily recognized. After specific immunoprecipitation and blotting with mAb 4G10 (anti-Ptyr), phosphorylated IL-2Rβ is identified on lysates from kit 225 cell line stimulated by IP130. c-myc induction which depends on IL-2Rβ phosphorylation is also observed after IP130 stimulation. STAT-3 and STAT-5 are not activated after IP130 stimulation since IL-2Rγ is not involved in IP130 interaction with Kit 225.

Example 9
Immunological Properties of IP130 and Use as Therapeutic Agent

IL-2Rβ chain is constitutively expressed by human NK cells from all donors studied (David et al., Blood 91:165–172, 1998). Monocytes only express IL-2Rγ chain. Other lymphocytes do not express neither IL-2Rβ nor IL-2Rα nor IL-2Rγ (David et al. 1998).

IP130 induces NK cells to enter into the cell cycle.

IP130 has been also tested on the generation of LAK in vitro. IP130 induces LAK activity as tested on K562 targets.

Figure 3A:
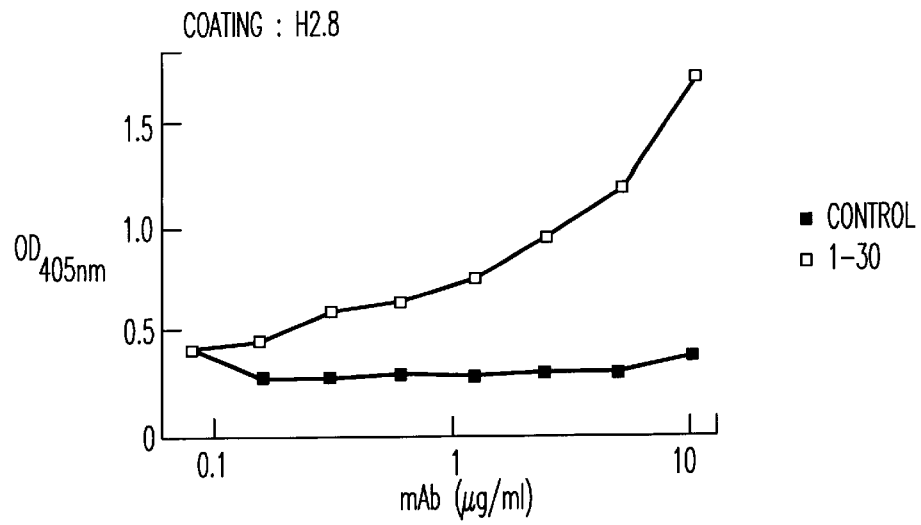
FIGS. 3A–C shows the binding of mAb H2-8 on peptide 1-30. Plates were coated with mAb H2-8 and were incubated with peptide 1-30 as described.
Figure 3B:
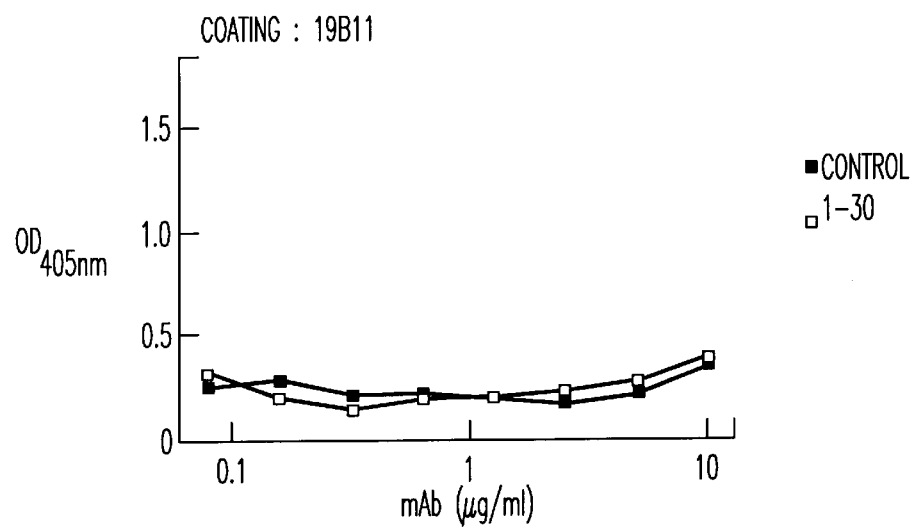
Figure 3C:
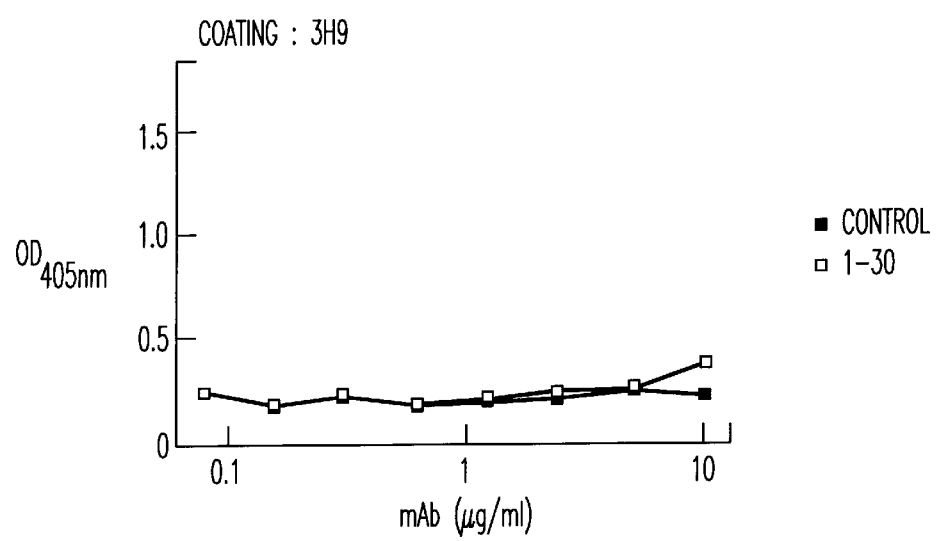
Figures 4A, 4B, 4C:
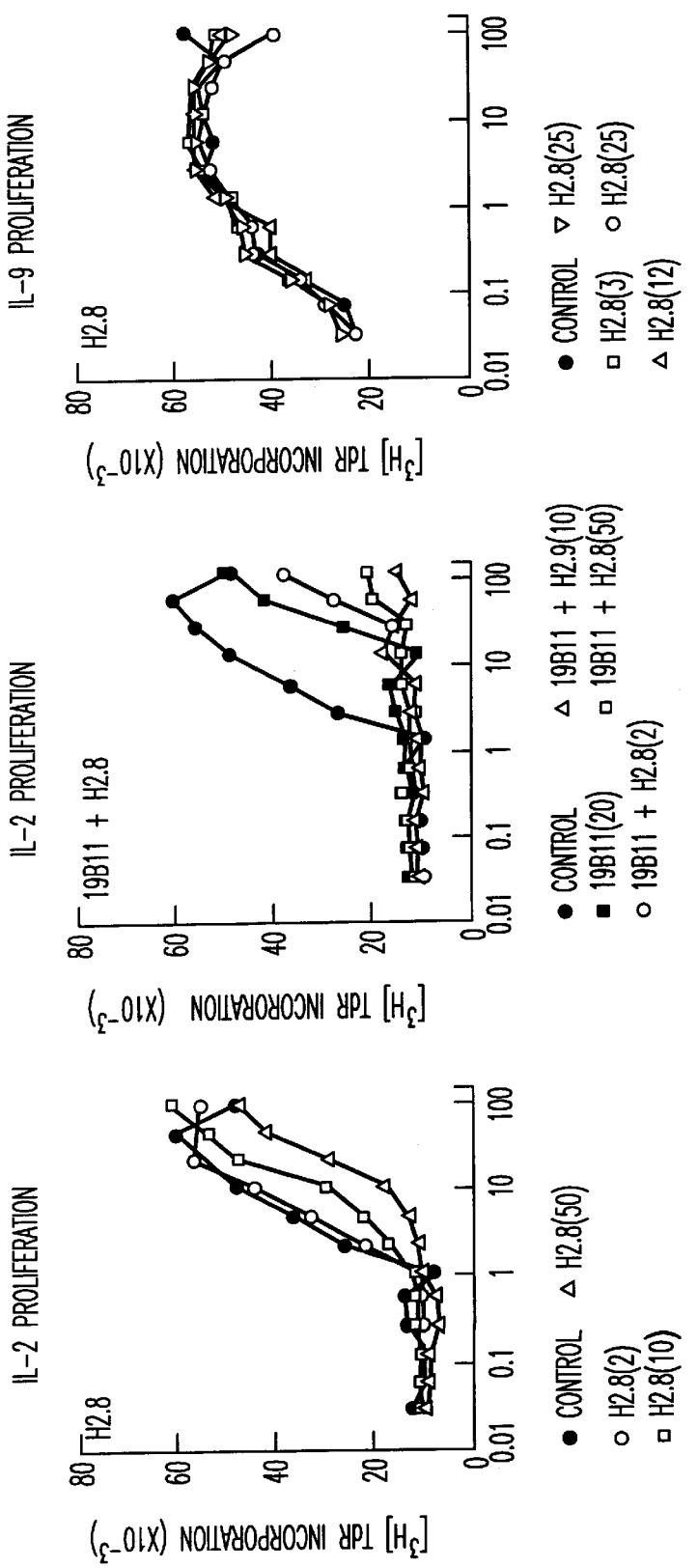
FIGS. 4A–F shows the biological effects of mAb H2-8 on IL-2 Pro$^{125}$. Different concentrations of IL-2 Pro$^{125}$ were tested on the proliferation of TS1β cells (IL-2Rα$^-$, human IL-2Rβ$^+$, mouse IL-2Rγ$^+$). The proliferation was measured by [$^{3H}$TdR] incorporation as indicated.
Figure 4F:
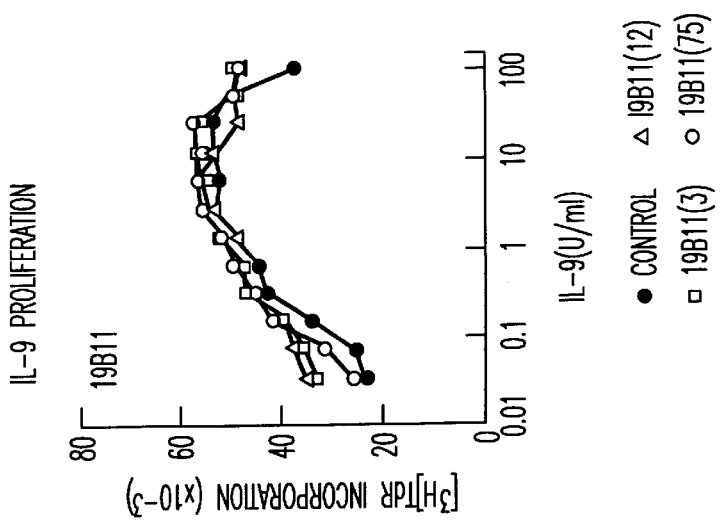
Figure 4E:
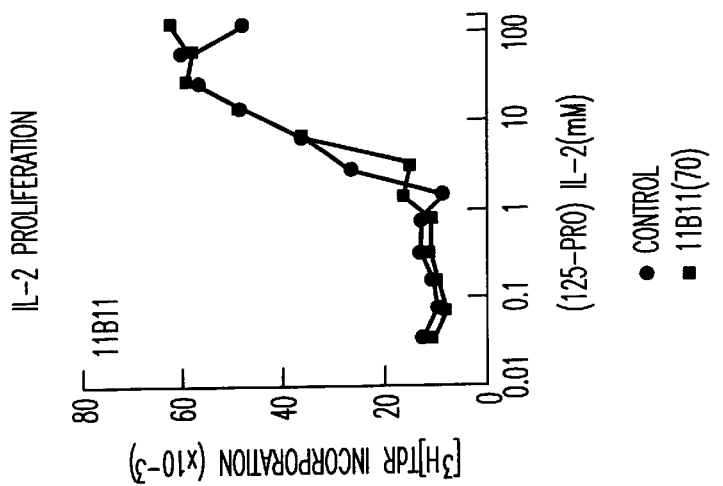
Figure 4D:
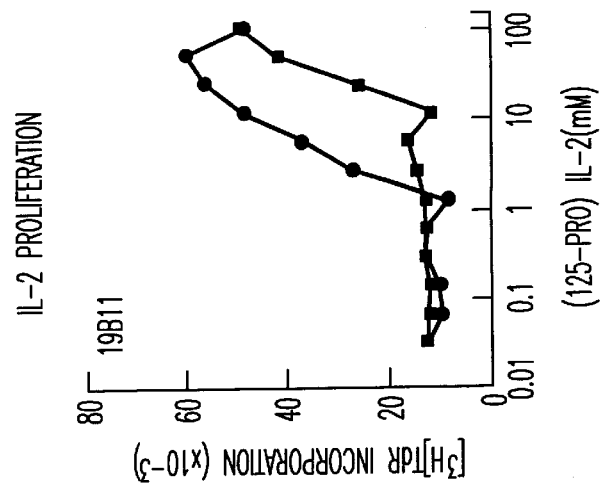

DISCUSSION mAb H2-8 was isolated after immunization with IL-2 peptide 1-30. It recognizes both IL-2 and peptide 1-30, but not the shorter peptides covering the same region (FIG. 2). This result suggests that mAb H-12–8 recognizes a conformational epitope on the N-termilal region of IL-2, and that this epitope is mimicked by the 1-30 peptide. Indeed, circular dichroism measurements reveal a significant fraction of α-helical structure for the 1-30 peptide. Furthermore, H2-8 can bind to peptide 1-30 even in the presence of mAb 19B11 (which recognizes a linear epitope within the non-helical part of the peptide 1-30), but does not recognize IL-2 mutants at position 20 (in the center of α-helix A) as determined by Western blot analysis or ELISA (FIG. 3 and other data not shown). The antibody also inhibits the bioactivity of IL-2 on TS1β cells (FIG. 4), whose proliferation is strictly dependent on the expression of the human IL-2Rβ chain. Taken together, these results demonstrate that mAb H2-8 recognizes an epitope around Asp20 of IL-2, a region that directly influences the interaction of the cytokine with IL-2Rβ.

Having now fully described the invention, it will be apparent to one of ordinary skill in the art that many changes and modifications can be made thereto without departing from the spirit or scope of the invention as set forth herein.

---

What is claimed as new and is desired to be secured by Letters Patent of the United States is:

1. A method of inducing in a patient an activity of IL-2, wherein said activity is selected from the group consisting of stimulation of CD4 cells, stimulation of CD8+ cells, stimulation of NK cells, antiviral activity, antitumor activity, induction of SHC phosphorylation and induction of SHC/MAPK pathway comprising administering to said patient an amount of a peptide not greater than 30 amino acids in length comprising SEQ ID NO:2 sufficient to induce said activities.

2. The method according to claim 1, wherein said activity is useful to treat metastatic melanoma, renal adenocarcinoma, melanoma, colorectal cancer, lung adenocarcinoma, breast cancer, ovarian cancer and viral infections cancer, infectious diseases, HIV infection or autoimmune disorders.

3. The method of claim 1, further comprising administering in admixture with the peptide a cytokine.

4. The method of claim 3, wherein the cytokine is IL-2, IL-4, IL-9, or IL-15.

5. The method of claim 3, wherein $1 \times 10^6$ international units of IL-2 is administered per injection.

6. The method of claim 1, wherein said the patient is infected with HIV and where the activity is stimulation of CD4 cells.

* * * * *

UNITED STATES PATENT AND TRADEMARK OFFICE
CERTIFICATE OF CORRECTION

PATENT NO.    : 6,168,785 B1
DATED         : January 2, 2001
INVENTOR(S)   : Jacques Theze et al.

It is certified that error appears in the above-identified patent and that said Letters Patent is hereby corrected as shown below:

<u>Column 4,</u>
Line 67, "11A" should read -- 8A --

<u>Column 5,</u>
Line 1, "11B" should read -- 8B --;
Line 2, "11C" should read -- 8C --;
Line 3, "11D" should read -- 8D --.

Signed and Sealed this

Thirtieth Day of September, 2003

JAMES E. ROGAN
*Director of the United States Patent and Trademark Office*

SEQUENCE LISTING

<160> NUMBER OF SEQ ID NOS: 2

<210> SEQ ID NO 1
<211> LENGTH: 93
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 1
atggctccga cgagcagctc caccaagaaa acccagctcc agctcgaaca cctgctgctg      60
gacctgcaga tgatcctgaa cggtatcaac aac                                  93

```
<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence:peptide

<400> SEQUENCE: 2

Met Ala Pro Thr Ser Ser Ser Thr Lys Lys Thr Gln Leu Gln Leu Glu
  1               5                  10                  15

His Leu Leu Leu Asp Leu Gln Met Ile Leu Asn Gly Ile Asn Asn
             20                  25                  30
```